US009532949B2

(12) United States Patent
Zeineldin

(10) Patent No.: US 9,532,949 B2
(45) Date of Patent: Jan. 3, 2017

(54) INTRAPERITONEALLY-ADMINISTERED NANOCARRIERS THAT RELEASE THEIR THERAPEUTIC LOAD BASED ON THE INFLAMMATORY ENVIRONMENT OF CANCERS

(75) Inventor: Reema Zeineldin, Shrewsbury, MA (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 14/233,527

(22) PCT Filed: Jul. 18, 2012

(86) PCT No.: PCT/US2012/047133
§ 371 (c)(1),
(2), (4) Date: Feb. 26, 2014

(87) PCT Pub. No.: WO2013/012891
PCT Pub. Date: Jan. 24, 2013

(65) Prior Publication Data
US 2014/0212479 A1    Jul. 31, 2014

Related U.S. Application Data

(60) Provisional application No. 61/509,251, filed on Jul. 19, 2011.

(51) Int. Cl.
*A61K 9/51* (2006.01)
*A61K 9/127* (2006.01)
(Continued)

(52) U.S. Cl.
CPC .............. *A61K 9/127* (2013.01); *A61K 9/0019* (2013.01); *A61K 31/704* (2013.01); *A61K 9/5115* (2013.01);
(Continued)

(58) Field of Classification Search
CPC ....................................................... A61K 9/127
See application file for complete search history.

(56) References Cited

U.S. PATENT DOCUMENTS 5,277,913 A    1/1994    Thompson et al.
5,753,263 A *  5/1998    Lishko et al. ................ 424/450
(Continued)

FOREIGN PATENT DOCUMENTS

JP        07502261 A    3/1995
JP        20100340 A    1/2010
(Continued)

OTHER PUBLICATIONS

J Liu, A Stace-Naughton, X Jiang, CJ Brinker. "Porous Nanoparticle Supported Lipid Bilayers (Protocells) as Delivery Vehicles." Journal of the American Chemical Society, vol. 131, 2009, pp. 1354-1355.*

(Continued)

*Primary Examiner* — Isaac Shomer
(74) *Attorney, Agent, or Firm* — Schwegman Lundberg & Woessner, P.A.

(57) ABSTRACT

In one embodiment, the invention provides a new design of nanocarrier compositions that release their therapeutic load specifically at intraperitoneal cancers' site. These nanocarriers are administered intraperitoneally and comprise a plurality of porous nanoparticulates that (a) are loaded with one or more pharmaceutically-active agents alone or in combination with imaging agents thus providing a theranostic value and (b) that are encapsulated by and that support a lipid bilayer which is disrupted upon contact with a reactive oxygen species generated within the environment of the cancer. In other embodiments, the invention provides methods of treatment and pharmaceutical compositions comprising nanocarriers as described herein.

15 Claims, 10 Drawing Sheets

(51) Int. Cl.
*A61K 31/704* (2006.01)
*A61K 9/00* (2006.01)

(52) U.S. Cl.
CPC ............ *A61K 9/5153* (2013.01); *Y10S 977/773* (2013.01); *Y10S 977/906* (2013.01); *Y10S 977/907* (2013.01); *Y10S 977/911* (2013.01)

(56) References Cited

U.S. PATENT DOCUMENTS

| | | | |
|---|---|---|---|
| 5,820,879 | A | 10/1998 | Fernandez et al. |
| 6,264,741 | B1 | 7/2001 | Brinker et al. |
| 6,350,464 | B1 * | 2/2002 | Dang ............................ 424/426 |
| 7,514,267 | B1 | 4/2009 | Lopez et al. |
| 8,298,677 | B2 | 10/2012 | Wiesner et al. |
| 8,734,816 | B2 | 5/2014 | Liu et al. |
| 8,992,984 | B1 | 3/2015 | Brinker et al. |
| 2002/0039594 | A1 | 4/2002 | Unger |
| 2004/0005352 | A1 | 1/2004 | Lopez et al. |
| 2004/0101822 | A1 | 5/2004 | Wiesner et al. |
| 2007/0037751 | A1 * | 2/2007 | Lange .................. C07K 14/575 514/4.9 |
| 2008/0095852 | A1 | 4/2008 | Kong et al. |
| 2008/0160313 | A1 | 7/2008 | Lopez et al. |
| 2008/0213377 | A1 | 9/2008 | Bhatia et al. |
| 2008/0279764 | A1 * | 11/2008 | Manganaro et al. ......... 424/1.11 |
| 2009/0324706 | A1 | 12/2009 | Mirkin et al. |
| 2010/0055167 | A1 | 3/2010 | Zhang et al. |
| 2010/0255103 | A1 | 10/2010 | Liong et al. |
| 2011/0097819 | A1 | 4/2011 | Groves et al. |
| 2011/0105995 | A1 | 5/2011 | Zhu et al. |
| 2011/0300186 | A1 | 12/2011 | Hellstrom et al. |
| 2014/0079774 | A1 | 3/2014 | Brinker et al. |
| 2014/0301951 | A1 | 10/2014 | Liu et al. |
| 2015/0010475 | A1 | 1/2015 | Brinker et al. |

FOREIGN PATENT DOCUMENTS

| | | |
|---|---|---|
| JP | 2011500520 A | 1/2011 |
| WO | 03016040 A1 | 2/2003 |
| WO | 03/055469 A1 | 7/2003 |
| WO | 2005/009602 A2 | 2/2005 |
| WO | 2010078569 A2 | 7/2010 |
| WO | WO 2010078569 A2 * | 7/2010 |
| WO | 2011/116226 A2 | 9/2011 |
| WO | 2012/149376 A2 | 11/2012 |
| WO | 2013/012891 A1 | 1/2013 |
| WO | 2013/056132 A2 | 4/2013 |
| WO | 2014/165608 A1 | 10/2014 |
| WO | 2014/165617 A1 | 10/2014 |
| WO | 2015/042268 A1 | 3/2015 |
| WO | 2015/042279 A1 | 3/2015 |

OTHER PUBLICATIONS

A Trafton. "Nanoparticles Target Ovarian Cancer." MIT News, Jul. 30, 2009, 2 printed pages (http://newsoffice.mit.edu/2009/ovarian-0730—accessed from web on Oct. 14, 2014).*
Scully R, Young R, Clement P. Tumors of the ovary, maldeveloped gonads, allopian tube, and broad ligament. Atlas of Tumor Pathology, ed. J. Rosia and L. Sobin. Vol Fascicle 23, 1998. Washington DC: Armed Forces Institute of Pathology.
Metzger-Filho O, Moulin C, D'Hondt V. First-line systemic treatment of ovarian cancer: a critical review of available evidence and expectations for future directions. Curr Opin Oncol, 2010;22(5):513-520.
Zeimet AG, et al. Pros and cons of intraperitoneal chemotherapy in the treatment of epithelial ovarian cancer. Anticancer Res, 2009;29(7):2803-2808.
Markman M, Walker JL. Intraperitoneal chemotherapy of ovarian cancer: a review, with a focus on practical aspects of treatment. J Clin Oncol, 2006;24(6):988-994.
Liu J, Matulonis UA. New advances in ovarian cancer. Oncology, 2010;24(8):721-728.
Filippovich IV, et al. Radiation-induced apoptosis in human ovarian carcinoma cells growing as a monolayer and as multicell spheroids. Int J Cancer, 1997;72(5):851-859.
Makhija S, et al. Taxol-induced bcl-2 phosphorylation in ovarian cancer cell monolayer and spheroids. Int J Oncol, 1999;14(3):515-521.
Bardies M, et al. Use of multi-cell spheroids of ovarian carcinoma as an intraperitoneal radio-immunotherapy model: uptake, retention kinetics and dosimetric evaluation. Int J Cancer, 1992;50(6):984-991.
Shield K, et al. Multicellular spheroids in ovarian cancer metastases: Biology and pathology. Gynecol Oncol, 2009;113(1):143-148.
Bapat SA. Human ovarian cancer stem cells. Reproduction, 2010;140(1):33-41.
Fong MY, Kakar SS. The role of cancer stem cells and the side population in epithelial ovarian cancer. Histol Histopathol, 2010;25(1):113-120.
Ponnusamy MP, Batra SK. Ovarian cancer: emerging concept on cancer stem cells. J Ovarian Res, 2008;1(1):4.
Freedman RS, et al. Peritoneal inflammation—A microenvironment for Epithelial Ovarian Cancer (EOC). J Transl Med, 2004;2(1):23.
Negus RP, et al. Quantitative assessment of the leukocyte infiltrate in ovarian cancer and its relationship to the expression of C—C chemokines. Am J Pathol, 1997;150(5):1723-1734.
Babior BM, et al. Investigating antibody-catalyzed ozone generation by human neutrophils. Proc Natl Acad Sci USA, 2003;100(6):3031-3034.
Wentworth P Jr, et al. Evidence for antibody-catalyzed ozone formation in bacterial killing and inflammation. Science, 2002;298(5601):2195-2199.
Wentworth P Jr, et al. Evidence for ozone formation in human atherosclerotic arteries. Science, 2003;302(5647):1053-1056.
Wentworth P Jr, et al. Antibody catalysis of the oxidation of water. Science, 2001;293(5536):1806-1811.
Freeman BA, Sharman MC, Mudd JB. Reaction of ozone with phospholipid vesicles and human erythrocyte ghosts. Arch Biochem Biophys, 1979;197(1):264-272.
Teige B, McManus TT, Mudd JB. Reaction of ozone with phosphatidylcholine liposomes and the lytic effect of products on red blood cells. Chem Phys Lipids, 1974;12(3):153-171.
Giamalva DH, Church DF, Pryor WA. Effect of bilayer structure on the rates of reaction of ozone with polyunsaturated fatty acids in phosphatidylcholine liposomes. Chem Res Toxicol, 1988;1(3):144-145.
Parikh AN. Membrane-substrate interface: phospholipid bilayers at chemically and topographically structured surfaces. Biointerphases, 2008;3(2):FA22.
Sanii B, Parikh AN. Patterning fluid and elastomeric surfaces using short-wavelength UV radiation and photogenerated reactive oxygen species. Annu Rev Phys Chem, 2008;59:411-432.
Yu C, Parikh AN, Groves JT. Direct patterning of membrane-derivatized colloids using in-situ UV-ozone photolithography. Adv Mater, 2005;17(12):1477-1480.
Steinbeck MJ, Khan AU, Karnovsky MJ. Intracellular singlet oxygen generation by phagocytosing neutrophils in response to particles coated with a chemical trap. J Biol Chem, 1992:267(19):13425-13433.
Steinbeck MJ, Khan AU, Karnovsky MJ. Extracellular production of singlet oxygen by stimulated macrophages quantified using 9,10-diphenylanthracene and perylene in a polystyrene film. J Biol Chem, 1993;268(21):15649-15654.
Piyasena ME, et al. Biosensors based on release of compounds upon distruption of lipid bilayers supoprted on porous microspheres. Biointerphases, 2008;3(2):38-49.
Chemburu S, et al. Biomimetic silica microspheres in biosensing. Molecules, 2010;15(3):1932-1957.
Toutier AL, Ladaviere C. An overview of lipid membrane supported by colloidal particles. Adv Colloid Interface Sci, 2007;133(1):1-21.
Jemal A, et al. Cancer Statistics. CA Cancer J Clin, 2010.
Auersperg N, et al. Ovarian surface epithelium: biology, endocrinology, and pathology. Endocr Rev, 2001;22(2):255-288.

(56) References Cited

OTHER PUBLICATIONS

Hudson LG, Zeineldin R, Stack MS. Phenotypic plasticity of neoplastic ovarian epithelium: unique cadherin profiles in tumor progression. Clin Exp Metastasis, 2008;25(6):643-655.

Lengyel E. Ovarian Cancer Development and Metastasis. Am J Pathol, 2010.

Heintz AP, et al. Carcinoma of the ovary. FIGO 6th Annual Report on the Results of Treatment in Gynecological Cancer. Int J Gynaecol Obstet, 2006;95 Suppl 1:S161-S192.

Williams TI, et al. Epithelial ovarian cancer: disease etiology, treatment, detection, and investigational gene, metabolite, and protein biomarkers. J Proteome Res, 2007;6(8):2936-2962.

Gubbels JA, et al. The detection, treatment, and biology of epithelial ovarian cancer. J Ovarian Res, 2010;3:8.

Shan W, Liu J. Inflammation: a hidden path to breaking the spell of ovarian cancer. Cell Cycle, 2009;8(19):3107-3111.

Guruvayoorappan C. Tumor versus tumor-associated macrophages: how hot is the link? Integr Cancer Ther, 2008;7(2):90-95.

Datta D, et al. Mechanism for antibody catalysis of the oxidation of water by singlet dioxygen. Proc Natl Acad Sci USA, 2002;99(5):2636-2641.

Lerner RA, Eschenmoser A. Ozone in biology. Proc Natl Acad Sci USA, 2003;100(6):3013-3015.

Brinkhorst J, Nara SJ, Pratt DA. Hock cleavage of cholesterol 5alpha-hydroperoxide: an ozone-free pathway to the cholesterol ozonolysis products identified in arterial plaque and brain tissue. J Am Chem Soc, 2008;130(37):12224-12225.

Uemi M, et al. Generation of cholesterol carboxyaldehyde by the reaction of singlet molecular oxygen [O2 (1Delta(g))] as well as ozone with cholesterol. Chem Res Toxicol, 2009;22(5):875-884.

Wentworth AD, et al. The ratio of cholesterol 5,6-secosterols formed from ozone and singlet oxygen offers insight to the oxidation of cholesterol in vivo. Chem Commun (Camb), 2009(21):3098-3100.

Drahl C. Probinh for In-Body Ozone: Molecule hunters need better traps to prove that a wily oxygen species is made in the flesh. Chem & Eng News, 2009;87(25):40-42.

Dedrick RL, et al. Pharmacokinetic rationale for peritoneal drug administration in the treatment of ovarian cancer. Cancer Treat Rep, 1978;62(1):1-11.

Howell SB. Pharmacologic principles of intraperitoneal chemotherapy for the treatment of ovarian cancer. Int J Gynecol Cancer, 2008;18 Suppl 1:20-25.

Travagli V, et al. A physicochemical investigation on the effects of ozone on blood. Int J Biol Macromol, 2007;41(5):504-511.

Burgassi S, et al. How much ozone bactericidal activity is compromised by plasma components? J Appl Microbiol, 2009;106(5):1715-1721.

Yamashita K, et al. Ozone production by amino acids contributes to killing of bacteria. Proc Natl Acad Sci USA, 2008;105(44):16912-16917.

Buranda T, et al. Biomimetic molecular assemblies on glass and mesoporous silica microbeads for biotechnology. Langmuir, 2003;19(5):1654-1663.

Zeineldin R, et al. Detection of membrane biointeractions based on fluorescence superquenching. Langmuir, 2008;24(8):4125-4131.

Green AE, Rose PG. Pegylated liposomal doxorubicin in ovarian cancer. Int J Nanomedicine, 2006;1(3):229-239.

Hawkins MJ, Soon-Shiong P, Desai N. Protein nanoparticles as drug carriers in clinical medicine. Adv Drug Deliv Rev, 2008;60(8):876-885.

Cannistra SA. Evaluating new regimens in recurrent ovarian cancer: how much evidence is good enough? J Clin Oncol, 2010;28(19):3101-3103.

Zeineldin R, Hudson LG. Epithelial cell migration in response to epidermal growth factor. Methods Mol Biol, 2006;327:147-158.

Edwards BS, et al. High-throughput cytotoxicity screening by propidium iodide staining. Curr Protoc Cytom, 2007: Chapter 9: Unit9 24.

Barua A, et al. Anti-tumor and anti-ovarian autoantibodies in women with ovarian cancer. Am J Reprod Immunol, 2007;57(4):243-249.

Luborsky JL, et al. Anti-tumor antibodies in ovarian cancer. Am J Reprod Immunol, 2005;54(2):55-62.

Piura B, Piura E. Autoantibodies to tumor-associated antigens in epithelial ovarian carcinoma. J Oncol, 2009:581939.

Pluedemann E. Silane Coupling Agents. Plenum Press, NY: 1982.

Ashley CE, et al., The targeted delivery of multicomponent cargos to cancer cells by nanoporous particle-supported lipid bilayers, Nature materials, 2011, 10:389-397.

Online supplement to Ashley CE, et al., The targeted delivery of multicomponent cargos to cancer cells by nanoporous particle-supported lipid bilayers, Nature materials, 2011, 10:389-397.

Ashley CE, et al., Delivery of Small Interfering RNA by Peptide-Targeted Mesoporus Silica Nanoparticle-Supported Lipid Bilayers, ACS Nano Mar. 2012, vol. 6, pp. 2174-2188.

Ashley CE. Development of Novel Bio/Nano Interfaces for Materials Science and Biomedical Applications (doctoral dissertation), University of New Mexico, Albuquerque, ProQuest publication 3409314 (Jun. 29, 2012).

Carroll NJ et al., Microparticles with Bimodal Nanoporosity Derived by Microemulsion Templating, Langmuir, 2009;25(23)13540-13544.

Dengler EC, et al., Mesoporous silica-supported lipid bilayers (protocells) for DAN cargo delivery to the spinal cord, Journal of Controlled Release, 2013;168:209-224.

Doshi DA, et al., Neutron Reflectivity Study of Lipid Membranes Assembled on Ordered Nanocompsite and Nanoporous Silica Thin Films, Langmuir, 2005;21:2865-2870.

Epler K, et al., Delivery of Ricin Toxin A-chain by Peptide-targeted mesoporous silica nanoparticle-supported lipid bilayers, Advanced Healthcare Materials, 2012:1:348-353.
Ferrari M. Cancer nanotechnology: Opportunities and Challenges, Nature 2005;5:161-171.
Gordon AN, et al., Recurrent Epithelial Ovarian Carcinoma: A Randomized Phase III Study of Pegylated Liposomal Doxorubicin Versus Toptecan, Journal of Clinical Oncology, 2001, 19(14): 3312-3322.
Irvine DJ. One Nanoparticle, One Kill, Nature Materials, 2011;10:342-343.
Jain RK. Barriers to Drug Delivery in Solid Tumors. Scientific American, 1994:58-65.
Kendall EL, et al., A New Class of Supported Lipid Bilayers: Lipid Coated Porous Silica Microspheres (bstract), 238th ACS National Meeting: Mar. 22-26, 2009.
Klein E, et al. "HFP" Fluorinated Cationic Lipids for Enhanced Lipoplex Stability and Gene Delivery; Biochonjugate Chemistry, 2010;21:360-371.
Liz, et al., Mesoporous Silica Nanoparticles in Biomedical Applications, Chemical Society Reviews, 2012;41: 2590-2605.
Li SD, et al., Tumor-targeted Delivery of siRNA by Self-Assembled Nanoparticles. Mol. Ther. 2007;16:163-169.
Liou GY, Peter S. Reactive oxygen species in cancer. Free Radical Research, 2010;44:479-496.
Liu J, et al, Electrostatically Mediated Liposome Fusion and Lipid Exchange with a Nanoparticle-Supported Bilayer for Control of Surface Charge, Drug Containment, and Delivery, J. Am. Chem. Soc, 2009;131:7567-7569.
Liu J, et al, Silica Nanoparticle supported lipid bilayers for gene delivery, Chem Commun, 2009; 5100-5102.
Lu Y, et al., Aerosol-Assisted Self Assembly of Mesostructure Spherical Nanoparticles, Nature, 1999, 398:223-226.
Rosenholm JM, et al., Towards multifunctional, targeted drug delivery systems using mesoporous silica nanoparticles—opportunities and challenges, Nanoscale, 2010;2:1870-1883.
Zhang Y, et al. ROS play a critical role in the differentiation of alternatively activated macrophages and the occurrence of tumor-associated macrophages. Cell Research, 2013;23:898-914.
Hsu HY, et al. Geldanamycin Interferes with the 90-kDa Heat Shock Protein, Affecting Lipopolysaccharide-Mediated Interleukin-1 Expression and Apoptosis within Macrophages. Molecular Pharmacology, 2007;71:344-356.

(56) References Cited

OTHER PUBLICATIONS

Martins De Lima-Salgado T, et al. Modulatory effect of fatty acids on fungicidal activity, respiratory burst and TNF-alpha and IL-6 production in J774 murine macrophages. British Journal of Nutrition, 2011;105:1173-1179.
Fernando De Souza L, et al. Regulation of LPS stimulated ROS production in peritoneal macrophages from alloxan-induced diabetic rats: involvement of high glucose and PPARgamma. Life Sciences, 2007;81:153-159.
Hsu HY, Wen MH. Lipopolysaccharide-mediated Reactive Oxygen Species and Signal Transduction in the Regulation of Interleukin-1 Gene Expression. The Journal of Biological Chemistry, 2002;277(25):22131-22139.
Freedman RS, et al. Peritoneal inflammation—A microenvironment for Epithelial Ovarian Cancer (EOC). Journal of Translational Medicine, 2004;2:23.
Saad AF, et al. Microenvironment and Pathogenesis of Epithelial Ovarian Cancer. Horm Canc, 2010;1:277-290.
Roszkowski K. Analysis of oxidative DNA damage/oxidative stress markers in patients with ovarian cancer. American Journal of Clinical and Experimental Medicine, 2013;1(2):40-43.
Chen J, et al. Dihydrodiol dehydrogenases regulate the generation of reactive oxygen species and the development of cisplatin resistance in human ovarian carcinoma cell.s Cancer Chemother Pharmacol, 2008;61:979-987.
Chan DW, et al. Loss of MKP3 mediated by oxidative stress enhances tumorigenicity and chemoresistance of ovarian cancer cells. Carcinogenesis, 2008;29(9)1742-1750.
Xia C, et al. Reactive Oxygen Species Regulate Angiogenesis and Tumor Growth through Vascular Endothelial Growth Factor. Cancer Res, 2007;67(22):10823-10830.
Storz P. Reactive Oxygen Species in Tumor Progression. Frontiers in Bioscience, 2005;10:1881-1896.
Australian Application Serial No. 2012284147, Amendment filed Dec. 16, 2015 , 17 pgs.
Chinese Application Serial No. 2012800456723, Office Action mailed Feb. 2, 2016, 19 pgs.
Chinese Application Serial No. 201280045672.3, Office Action mailed May 6, 2015, 6 pgs.
Chinese Application Serial No. 201280045672.3, Response filed Jun. 16, 2016 to Office Action mailed Feb. 2, 2016, (English Translation of Claims), 28 pgs.
Chinese Application Serial No. 201280045672.3, Response filed Sep. 2, 2015 to Office Action mailed May 6, 2015, 16 pgs.
Chinese Application Seriai No. 2012800456723, Supplemental Declaration of Reema Zeineldin, Ph.D, mailed Feb. 4, 2016, 6 pgs.
Eurasian Application Serial No. 201490302/28, Office Action mailed Mar. 10, 2016, 4 pgs.
Eurasian Application Serial No. 201490302/28, Office Action mailed Apr. 8, 2014, 2 pgs.
Eurasian Application Serial No. 201490302/28, Office Action mailed Jul. 8, 2015, 4 pgs.
Eurasian Application Serial No. 201490302/28, Response filed Dec. 8, 2015, 24 pgs.
European Application Serial No. 12815024.0, Amendment filed Mar. 27, 2014, 10 pgs.
European Application Serial No. 12815024.0, Amendment filed Oct. 21, 2015, 11 pgs.
European Application Serial No. 12815024.0, Declaration of Reema Zeineldin, PH.D. mailed Apr. 28, 2015, 19 pgs.
European Application Serial No. 12815024.0, Response filed May 18, 2016, 16 pgs.
European Application Serial No. 12815024.0, Response filed Feb. 17, 2014, 16 pgs.
European Application Serial No. 12815024.0, Search Report mailed Mar. 31, 2015, 12 pgs.
International Application Serial No. PCT/US2012/047133, International Preliminary Report on Patentability mailed Jan. 21, 2014, 9 pgs.
International Application Serial No. PCT/US2012/047133, International Search Report mailed Nov. 16, 2012, 5 pgs.
International Application Serial No. PCT/US2012/047133, Written Opinion mailed Nov. 16, 2012, 8 pgs.
Japanese Application Serial No. 2014-521722, Office Action mailed May 2, 2016, Without English Translation, 4 pgs.
Scientists Develop High-Capacity Nanoparticles for Targeted Delivery of Drug Cocktails, Genetic Engineering & Biotechnology News, Apr. 18, 2011, 2 pgs.
Chinese Application Serial No. 201280045672.3, Office Action mailed Oct. 17, 2016, W/English Translation, 9 pgs., English portions of reference considered by examiner.

\* cited by examiner

OSE — Shedding of cells — Intraperitoneal Dissemination as SCs & MCAs $$x\,{}^1O_2^* + yH_2O \leftrightarrow [H_2O_3(y-1)H_2O] \rightarrow O_3 + H_2O_2 + (x-1)\,{}^3O_2$$

Evaluate different lipid composition of SLB   Ozone generation causes lysis of SLB & release of fluorescein →Detect decrease in spheres' fluorescence by flow cytometry FIGURE 12
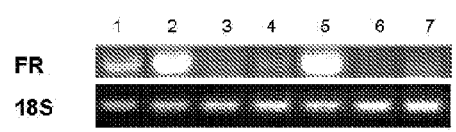
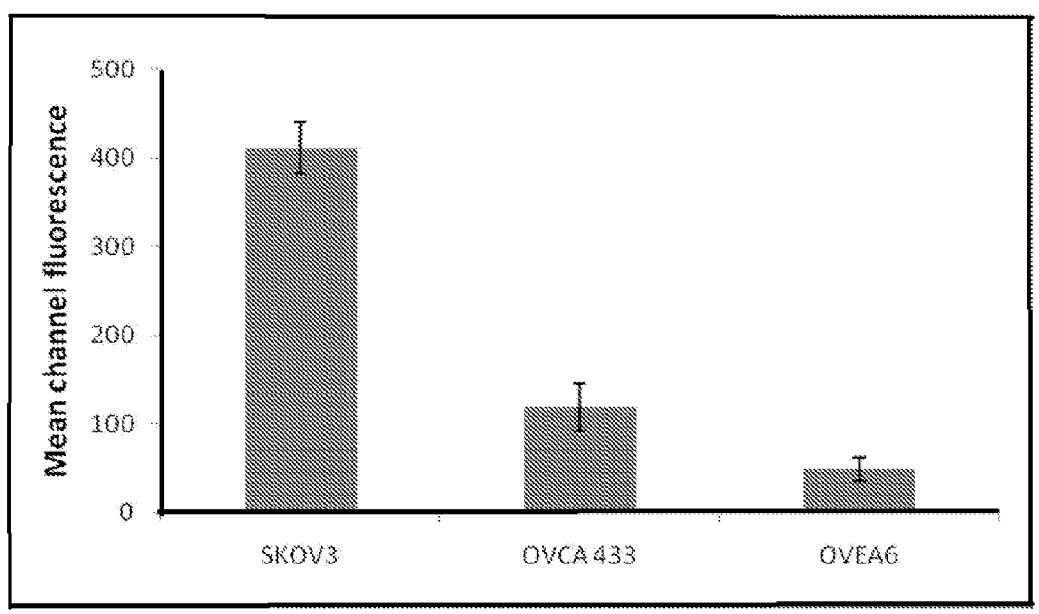

INTRAPERITONEALLY-ADMINISTERED NANOCARRIERS THAT RELEASE THEIR THERAPEUTIC LOAD BASED ON THE INFLAMMATORY ENVIRONMENT OF CANCERS

RELATED APPLICATIONS

This application claims priority from and is a U.S. national stage application of International Patent Application No. PCT/US2012/047133 filed Jul. 18, 2012, and entitled "Intraperitoneally-Administered Nanocarriers that Release Their Therapeutic Load Based on the Inflammatory Environment of Cancers, which claims priority from U.S. Provisional Application Ser. No. 61/509,251, filed Jul. 19, 2011, and entitled "Novel Nanotechnology Platform for Treatment of Peritoneal Cancers", the entire contents of which are hereby incorporated by reference.

FIELD OF THE INVENTION

In one embodiment, the invention provides a new design of nanocarriers that release their therapeutic load specifically at intraperitoneal cancers' site. These nanocarriers are administered intraperitoneally and comprise a plurality of porous nanoparticulates that (a) are loaded with one or more pharmaceutically-active agents alone or in combination with imaging agents thus providing a theranostic value and (b) that are encapsulated by and that support a lipid bilayer which is disrupted upon contact with a reactive oxygen species generated within the environment of the cancer.

In other embodiments, the invention provides methods of treatment and pharmaceutical compositions that use nanocarriers as described herein.

BACKGROUND OF THE INVENTION

Ovarian carcinoma is the leading cause, of death from gynecologic malignancy, resulting in approximately 21,880 estimated new cases in 2010 with an estimated 13,850 deaths in 2010 in the USA [30]. Most OVCA arises from the ovarian surface epithelium (OSE) [31] and clinically, it often involve the ovary and omentum, with diffuse, multi-focal intraperitoneal metastases and malignant ascites [1]. Metastasis of OVCA (FIG. 1) involves shedding of cells from the primary OVCA either as single cells (SCs) or as spheroids or multicellular aggregate (MCAs) that later interact with mesothelial cells that line the inner surface of the peritoneum and disseminate to adjacent pelvic organs [9, 32, 33]. Most OVCA patients (approximately 75%) are diagnosed too late with disseminated intra-abdominal disease (stage IV) and because of this late diagnosis they have low survival rates [34]. For therapy, patients usually undergo cytoreductive surgery followed by the administration of the standard first line chemotherapeutic combination regimen of carboplatin and paclitaxel [2, 5, 35]. Nevertheless, most of the patients will eventually suffer from therapeutic resistance and undergo relapse of OVCA [35, 36].

Evidence points to the role of inflammation in both ovulation and OVCA [13, 37]. It appears that the inflammation within the peritoneal microenvironment of OVCA contributes to progression of OVCA due to immune cell infiltration into the OVCA microenvironment [13, 14]. It has been reported that in OVCA leukocytes are present within the ascitic fluid including activated macrophages and T cells and to a lower numbers natural killer cells, B cells, and mast cells [14]. These activated immune cells produce reactive oxygen species and secrete cytokines and angiogenic and growth factors that promote OVCA progression [38].

Antibodies, regardless of their source or antigenic specificity, and T cell receptors catalyze the formation of ozone (a molecule with the chemical signature of ozone) through water oxidation in presence of singlet molecular oxygen (FIG. 2) and cause bacterial toxicity [16, 18, 39, 40]. In vivo, this reaction occurs due to activated immune cells which are the source of singlet molecular oxygen[16, 17]. In a tube singlet molecular oxygen is generated by adding a photosensitizer and exposing the tube contents to near UV irradiation, i.e. employing a photochemical source [16, 18]. However in vivo singlet molecular oxygen is known to be generated by activated neutrophils [25, 26]. For example, ozone was formed in vivo in a reversed-passive Arthus reaction generated through intradermal injections in rats using albumin and anti-albumin antibody were ozone was detected in the inflammatory legions [16]. Moreover, Wentworth and coworkers reported that ozone was formed in vivo in atherosclerotic plaques in addition to in vitro atherosclerotic plaques in presence of activated leukocytes with generation of atheronals as products of cholesterol ozonolysis [17]. On the other hand, that study has been under debate as the atheronals detected in it as unique products of cholesterol ozonolysis could also be generated, in addition to ozone, through singlet oxygen[41, 42]. Nevertheless, Wentworth and coworkers re-evaluated samples from their first study and demonstrated that the ratios of obtained products indicate involvement of ozone rather than singlet oxygen in formation of the detected atheronals [43, 44].

Ozone, and products of ozonation are known to cause disruption and lysis of phospholipid bilayers and cells [19-21]. Furthermore, reactive oxygen species and ozone cause photolysis of organic molecules and of phospholipids in lipid bilayers supported on spherical or planar platforms [22-24]. If these bilayers are part of liposomes or are supported on porous spheres, then their disruption will result in leakage of their contents such as chemotherapeutic agents.

To summarize, ovarian cancer (OVCA) is a peritoneal disease as its metastasis and dissemination to other organs takes place through the peritoneal cavity [1]. Thus intraperitoneal (IP) administration of chemotherapeutic agents treats local and disseminated OVCA as it is confined to the peritoneum. Recently the efficacy of IP chemotherapy of OVCA has been demonstrated when done alone or in combination with intravenous chemotherapy [2-5]. This is probably due to direct delivery of drugs to several types of peritoneal OVCA cells that play a role in chemotherapeutic resistance such as cancer stem cells and spheroids [6-12].

The peritoneal microenvironment of OVCA is an inflammatory one due to the infiltration of immune cells that produce reactive oxygen species and secrete factors that promote tumor progression [13, 14]. Recent reports demonstrated that ozone is generated in vivo in inflammatory diseases [15-17]. This production of ozone is the direct outcome of an antibody's oxidative catalytic activity [16, 18]. Antibodies, regardless of their source or antigenic specificity, catalyze the generation of ozone and peroxide by a water oxidation pathway [16, 18]. The only requirement for antibodies to mediate this reaction is a source of singlet molecular oxygen, which is provided in vitro by near UV irradiation in presence of a photosensitizer [16, 18]. In vivo, the only requirement for this reaction to occur is the presence of activated immune cells which are the source of singlet molecular oxygen in addition to mediating the water oxidation pathway and generating ozone [16, 17].

Ozone and other ROS are known to cause peroxidation of phospholipid bilayers and formation of free radicals resulting in lysis of lipid bilayers made of phospholipids [19-24]. If these bilayers are part of liposomes or are supported on porous nanospheres, then their disruption by ROS results in leakage of their contents such as chemotherapeutic agents.

Thus, the need exists for a nanocarrier for IP therapy of OVCA that can (1) utilize generation of ROS mediated by activated immune cells in inflammatory diseases like OVCA [16, 17, 25, 26]; (2) enable ROS to disrupt lipid bilayers whether free or supported on spherical or planar platforms [19-24]; and (3) use robust supported lipid bilayer membrane assemblies on porous nanoparticles that have capabilities to entrap chemotherapeutic agents [27-29].

SUMMARY OF THE INVENTION

In one embodiment, the invention provides a new design of nanocarriers that release their therapeutic load specifically at intraperitoneal cancers' site. These nanocarriers as compositions are administered directly into a site of activity such as a cancer or tumor and preferably, intraperitoneally and comprise a plurality of porous nanoparticulates that (a) are loaded with one or more pharmaceutically-active agents alone or in combination with imaging agents thus providing a theranostic value and (b) that are encapsulated by and that support a lipid bilayer which is disrupted upon contact with a reactive oxygen species generated within the environment of the cancer.

Preferably: (1) the nanoparticulates are comprised of one or more compositions selected from the group consisting of silica, a biodegradable polymer, a sol-gel, a metal and a metal oxide; and (2) the lipid bilayer undergoes maximum disruption when contacted by at least one reactive oxygen species.

In an another preferred embodiment,
(a) the nanocarrier includes at least one anticancer agent;
(b) less than around 10% to around 20%, or less than around 11% to around 19%, or less than around 12% to around 18%, or less than around 13% to around 17% or less than around 14% to around 16%, or less than around 15% of the anticancer agent is released from the porous nanoparticulates in the absence of a reactive oxygen species; and
(c) upon disruption of the lipid bilayer as a result of contact with a reactive oxygen species, the porous nanoparticulates release an amount of anticancer agent that is approximately equal to around 60% to around 80%, or around 65% to around 75%, or around 66% to around 74%, or around 67% to around 73%, or around 68% to around 72%, or around 69% to around 71%, or around 70% of the amount of anticancer agent that would have been released had the lipid bilayer been lysed with 5% (w/v) Triton X-100.

In other preferred embodiments:
(a) the nanoparticulates are comprised of a composition selected from the group consisting of silica, a biodegradable polymer, a sol-gel, a metal and a metal oxide;
(b) the nanocarrier contain at least one pharmaceutically-active agent used to treat cancers, e.g. at least one anti-cancer agent selected from the group consisting of doxorubicin, melphalan, bevacizumab, dactinomycin, cyclophosphamide, amifostine, etoposide, gemcitabine, altretamine, topotecan, cyclophosphamide, taxane-based chemotherapeutic agents including paclitaxel/taxol and docetaxol, among others or a platinum-based chemotherapeutic agent, including carboplatin or cisplatin, and taxol;

(c) the lipid bilayer is disrupted in vivo upon contact with a reactive oxygen species (ROS) selected from the group consisting of ozone ($O_3$), hydrogen peroxide, hypochlorite ion, hydroxyl radical, superoxide anion ($O_2^-$), and peroxynitrite; and
(d) the nanocarrier is administered to the subject, directly into the cancer/tumor or preferably intraperitoneally to the peritoneum of a subject suffering from peritoneal cancer.

In another embodiment, the invention provides a method of treating a subject who suffers from a cancer, the method comprising administering directly at a site of activity including a site of a cancer/tumor, or preferably intraperitoneally (IP) to the subject a pharmaceutically effective amount of a nanocarrier as described herein. In a preferred embodiment, the nanocarriers are administered to treat a subject who suffers from a peritoneal cancer.

In still another embodiment, the invention provides a pharmaceutical composition that comprises a nanocarrier as described herein and that is formulated for intraperitoneal injection.

These and other embodiments of the invention are described further in the detailed description of the invention.

BRIEF DESCRIPTION OF THE FIGURES

FIG. 12. Expression of an ovarian cancer specific receptor, folate receptor alpha (FRα) in various ovarian cancer cells. Top: RT-PCR 1=OVCA 433, 2=SKOV-3, 3=OVCA 420, 4=OVCA 429, 5=OVCA 432, 6=DOV13, and 7=OVEA6. Bottom: Flow cytometry for FRα in SKOV3, OVCA 433, and OVEA6 using mouse anti-FRα (Sig-3619), and anti-mouse-FITC. Flow cytometry confirmed that protein expression of FRα is high is SKOV-3.

DETAILED DESCRIPTION OF THE INVENTION

Figures 1, 2:
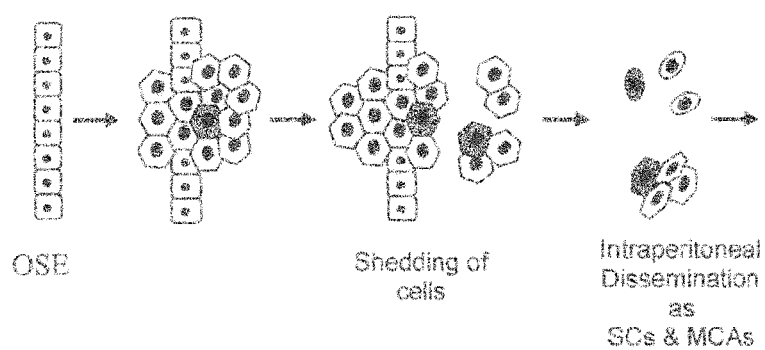
FIG. 1: Steps involved in epithelial ovarian carcinogenesis. Gray cells are cancer stem cells (CSCs), OSE=ovarian surface epithelium, SCs=single cells, MCAs=multicellular aggregates or spheroids.
FIG. 2. Equation of the water oxidation reaction, catalyzed by antibodies and T cell receptors [40], with singlet oxygen and water as substrates and ozone, hydrogen peroxide and triplet oxygen as products, with a dihydrogen trioxide intermediate.

The following terms are used throughout the specification to describe the present invention. Where a term is not given a specific definition herein, that term is to be given the same meaning as understood by those of ordinary skill in the art. The definitions given to the disease states or conditions which may be treated using one or more of the compounds according to the present invention are those which are generally known in the art.

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

Molecular oxygen (dioxygen; $O_2$) is essential for the survival of all aerobic organisms. Aerobic energy metabolism is dependent on oxidative phosphorylation, a process by which the oxidoreduction energy of mitochondrial electron transport (via a multicomponent NADH dehydrogenase enzymatic complex) is converted to the high-energy phosphate bond of ATP. $O_2$ serves as the final electron acceptor for cytochrome-c oxidase, the terminal enzymatic component of this mitochondrial enzymatic complex, that catalyzes the four-electron reduction of $O_2$ to $H_2O$. Partially reduced and highly reactive metabolites of $O_2$ may be formed during these (and other) electron transfer reactions. These $O_2$ metabolites include superoxide anion ($O_2^-$) and hydrogen peroxide ($H_2O_2$), formed by one- and two-electron reductions of $O_2$, respectively. In the presence of transition metal ions, the even more reactive hydroxyl radical (OH.) can be formed. These partially reduced metabolites of $O_2$ are often referred to as "reactive oxygen species" (ROS) due to their higher reactivities relative to molecular $O_2$.

"Reactive oxygen species" (ROS) include, but are not limited to, the reactive oxygen species described in Afanas'ev, "Reactive Oxygen Species Signaling in Cancer: Comparison with Aging", *Aging Dis.* 2011 June; 2(3): 219-230. Exemplary reactive oxygen species (ROS) include, but are not limited to, ozone ($O_3$), hydrogen peroxide, hypochlorite ion, hydroxyl radical, superoxide anion ($O_2^-$), and peroxynitrite.

The term "nanoparticulate" refers to a multiparticulate in which the "effective average particle size" of the particles therein is less than about 2,000 nm (2 microns) in diameter. A composition comprising a nanoparticulate is described herein as a "nanoparticulate composition".

The terms "nanoparticulate" and "porous nanoparticulate" are used interchangeably herein and such particles may exist in a crystalline phase, an amorphous phase, a semi-crystalline phase, a semi amorphous phase, or a mixture thereof.

A nanoparticle may have a variety of shapes and cross-sectional geometries that may depend, in part, upon the process used to produce the particles. In one embodiment, a nanoparticle may have a shape that is a sphere, a rod, a tube, a flake, a fiber, a plate, a wire, a cube, or a whisker. A nanoparticle may include particles having two or more of the aforementioned shapes. In one embodiment, a cross-sectional geometry of the particle may be one or more of circular, ellipsoidal, triangular, rectangular, or polygonal. In one embodiment, a nanoparticle may consist essentially of non-spherical particles. For example, such particles may have the form of ellipsoids, which may have all three principal axes of differing lengths, or may be oblate or prelate ellipsoids of revolution. Non-spherical nanoparticles alternatively may be laminar in form, wherein laminar refers to particles in which the maximum dimension along one axis is substantially less than the maximum dimension along each of the other two axes. Non-spherical nanoparticles may also have the shape of frusta of pyramids or cones, or of elongated rods. In one embodiment, the nanoparticles may be irregular in shape. In one embodiment, a plurality of nanoparticles may consist essentially of spherical nanoparticles.

The phrase "effective average particle size" as used herein to describe a multiparticulate (e.g., a porous nanoparticulate) means that at least 50% of the particles therein are of a specified size. Accordingly, "effective average particle size of less than about 2,000 nm in diameter" means that at least 50% of the particles therein are less than about 2000 nm in diameter. In certain embodiments, nanoparticulates have an effective average particle size of less than about 2,000 nm (i.e., 2 microns), less than about 1,900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods. "$D_{50}$" refers to the particle size below which 50% of the particles in a multiparticulate fall. Similarly, "$D_{90}$" is the particle size below which 90% of the particles in a multiparticulate fall.

In certain embodiments, the porous nanoparticulates are comprised of one or more compositions selected from the group consisting of silica, a biodegradable polymer, a sol-gel, a metal and a metal oxide.

Porous nanoparticulates used in nanocarriers of the invention include mesoporous silica nanoparticles and core-shell nanoparticles.

The porous nanoparticulates can also be biodegradable polymer nanoparticulates comprising one or more compositions selected from the group consisting of aliphatic polyesters, poly(lactic acid) (PLA), poly(glycolic acid) (PGA), co-polymers of lactic acid and glycolic acid (PLGA), polycarprolactone (PCL), polyanhydrides, poly(ortho)esters, polyurethanes, poly(butyric acid), poly(valeric acid), poly(lactide-co-caprolactone), alginate and other polysaccharides, collagen, and chemical derivatives thereof, albumin, a hydrophilic protein, zein (a corn storage protein), a prolamine, a hydrophobic protein, and copolymers and mixtures thereof.

Alternatively, the porous nanoparticles can be comprised of a sol-gel mixture formed by the addition of an organic solvent and metal alkoxide in the presence of water. In a purely illustrative embodiment, the metal oxide of the metal alkoxide is Ti, Zr, Sn, B, Al and Y may be used and in still other embodiments, nanoparticles made of gold or silver also may be employed.

In other illustrative embodiments, the porous nanoparticles are comprised of a sol-gel mixture formed by the addition of an organic solvent and a Si alkoxide in the presence of water.

In still other embodiments, the porous nanoparticles each comprise a core having a core surface that is essentially free of silica, and a shell attached to the core surface, wherein the core comprises a transition metal compound selected from the group consisting of oxides, carbides, sulfides, nitrides, phosphides, borides, halides, selenides, tellurides, tantalum oxide, iron oxide or combinations thereof.

The silica nanoparticles used in the present invention can be, for example, mesoporous silica nanoparticles and core-shell nanoparticles. The nanoparticles may incorporate an absorbing molecule, e.g. an absorbing dye. Under appropriate conditions, the nanoparticles emit electromagnetic radiation resulting from chemiluminescence.

Mesoporous silica nanoparticles can be e.g. from around 5 nm to around 500 nm in size, including all integers and ranges there between. The size is measured as the longest axis of the particle. In various embodiments, the particles are from around 10 nm to around 500 nm and from around 10 nm to around 100 nm in size. The mesoporous silica nanoparticles have a porous structure, with at least one pore and preferably, a number of pores opening at the surface of the nanoparticle. The pores can be from around 1 to around 20 nm in diameter, including all integers and ranges there between. In one embodiment, the pores are from around 1 to around 10 nm in diameter. In one embodiment, around 90% of the pores are from around 1 to around 20 nm in diameter. In another embodiment, around 95% of the pores are around 1 to around 20 nm in diameter.

The mesoporous nanoparticles can be synthesized according to methods known in the art. In one embodiment, the nanoparticles are synthesized using sol-gel methodology where a silica precursor or silica precursors and a silica precursor or silica precursors conjugated (i.e., covalently bound) to absorber molecules are hydrolyzed in the presence of templates in the form of micelles. The templates are formed using a surfactant such as, for example, hexadecyltrimethylammonium bromide (CTAB). It is expected that any surfactant which can form micelles can be used.

The core-shell nanoparticles comprise a core and shell. The core comprises silica and an absorber molecule. The absorber molecule is incorporated in to the silica network via a covalent bond or bonds between the molecule and silica network. The shell comprises silica.

In one embodiment, the core is independently synthesized using known sol-gel chemistry, e.g., by hydrolysis of a silica precursor or precursors. The silica precursors are present as a mixture of a silica precursor and a silica precursor conjugated, e g, linked by a covalent bond, to an absorber molecule (referred to herein as a "conjugated silica precursor"). Hydrolysis can be carried out under alkaline (basic) conditions to form a silica core and/or silica shell. For example, the hydrolysis can be carried out by addition of ammonium hydroxide to the mixture comprising silica precursor(s) and conjugated silica precursor(s).

Silica precursors are compounds which under hydrolysis conditions can form silica. Examples of silica precursors include, but are not limited to, organosilanes such as, for example, tetraethoxysilane (TEOS), tetramethoxysilane (TMOS) and the like.

The silica precursor used to form the conjugated silica precursor has a functional group or groups which can react with the absorbing molecule or molecules to form a covalent bond or bonds. Examples of such silica precursors include, but is not limited to, isocyanatopropyltriethoxysilane (ICPTS), aminopropyltrimethoxysilane (APTS), mercaptopropyltrimethoxysilane (MPTS), and the like.

In one embodiment, an organosilane (conjugatable silica precursor) used for forming the core has the general formula $R_{4n}SiX_n$, where X is a hydrolyzable group such as ethoxy, methoxy, or 2-methoxy-ethoxy; R can be a monovalent organic group of from 1 to 12 carbon atoms which can optionally contain, but is not limited to, a functional organic group such as mercapto, epoxy, acrylyl, methacrylyl, or amino; and n is an integer of from 0 to 4. The conjugatable silica precursor is conjugated to an absorber molecule and subsequently co-condensed for forming the core with silica precursors such as, for example, TEOS and TMOS. A silane used for forming the silica shell has n equal to 4. The use of functional mono-, bis- and tris-alkoxysilanes for coupling and modification of co-reactive functional groups or hydroxy-functional surfaces, including glass surfaces, is also known, see Kirk-Othmer, Encyclopedia of Chemical Technology, Vol. 20, 3rd Ed., J. Wiley, N.Y.; see also E. Pluedemann, Silane Coupling Agents, Plenum Press, N.Y. 1982. The organo-silane can cause gels, so it may be desirable to employ an alcohol or other known stabilizers. Processes to synthesize core-shell nanoparticles using modified Stoeber processes can be found in U.S. patent application Ser. Nos. 10/306,614 and 10/536, 569, the disclosure of such processes therein are incorporated herein by reference.

In certain embodiments of a nanocarrier of the invention, the lipid bilayer is comprised of one or more lipids selected from the group consisting of phospholipids including phosphatidyl cholines and other phospholipids such as DOTAP and cholesterol.

In certain additional embodiments, the lipid bilayer is comprised of one or more phospholipids, including phosphatidyl-cholines (PCs), wherein said phospholipid is selected from the group consisting of 1,2-dimyristoyl-sn-glycero-3-phosphocholine (DMPC), 1,2-dioleoyl-3-trimethylammonium-propane (DOTAP), 1-palmitoyl-2-oleoyl-sn-glycero-3-phosphocholine (POPC), egg PC (preferably, at least egg PC) and a lipid mixture comprising between about about 25% to about 55% or more, about 35% to about 50%, about 36% to about 49%, about 37% to about 48%, about 40% (often less than about 50%) of egg PC, about 50% to about 70%, about 51% to about 69%, or about 52% to about 68%, or about 53% to about 67%, or about 54% to about 66%, or about 55% to about 65%, or about 56% to about 64%, or about 57% to about 63%, or about 58% to about 62%, or about 59% to about 61%, or about 60%, of one or more unsaturated phospholipid, DMPC [14:0] having a carbon length of 14 and no unsaturated bonds, 1,2-dipalmitoyl-sn-glycero-3-phosphocholine_(DPPC) [16:0], 1,2-distearoyl-sn-glycero-3-phosphocholine (DSPC) [18:0], 1,2-dioleoyl-sn-glycero-3-phosphocholine (DOPC) [18:1 (Δ9-Cis)], POPC [16:0-18:1], and DOTAP [18:1], or mixtures thereof.

In still other embodiments:
(a) the lipid bilayer is comprised of a mixture of (1) egg PC, and (2) one or more phospholipids selected from the group consisting of 1,2-dimyristoyl-sn-glycero-3-phosphocholine (DMPC), 1,2-dioleoyl-3-trimethylammonium-propane (DOTAP), 1-palmitoyl-2-oleoyl-sn-glycero-3-phosphocholine (POPC), and a lipid mixture comprising between about about 25% to about 55% or more, about 35% to about 50%, about 36% to about 49%, about 37% to about 48%, about 40% to about 49% (often less than about 50% of the egg PC), about 50% to about 70% or about 51% to about 69%, or about 52% to about 68%, or about 53% to about 67%, or about 54% to about 66%, or about 55% to about 65%, or about 56% to about 64%, or about 57% to about 63%, or about 58% to about 62%, or about 59% to about 61%, or about 60%, of one or more unsaturated phospholipids, preferably an unsaturated phosphatidyl choline, DMPC [14:0] having a carbon length of 14 and no unsaturated bonds, 1,2-dipalmitoyl-sn-glycero-3-phosphocholine (DPPC) [16:0], 1,2-distearoyl-sn-glycero-3-phosphocholine (DSPC) [18:0], 1,2-dioleoyl-sn-glycero-3-phosphocholine (DOPC) [18:1 (Δ9-Cis)], POPC [16:0-18:1] and DOTAP [18:1]; and wherein
(b) the molar concentration of egg PC in the mixture is between about 10% to about 75% or about 15% to about 70%, or about 25% to about 68%, or about 30% to about 67%, or about 34% to about 66%, or about 40% to about 65%, or about 45% to about 64%, or about 47% to about 63%, or about 48% to about 62%, or about 49% to about 61%, or about 50% to about 60%, or about 51% to about 59%, or about 52% to about 58%, or about 53% to about 57%, or about 54% to about 62%, or about 55% to about 65%, or about 56% to about 64%, or about 57% to about 63%, or about 58% to about 62%, or about 29% to about 31%, or about 30% and the remaining portion of the bilayer comprising the In still other preferred aspects, the lipid bilayer comprises egg PC at a molar concentration of about 40% to about 60% and at least one additional phospholipid set forth above in a molar concentration of about 40% to about 60%. In certain preferred embodiments the lipid bilayer comprises egg PC at a molar concentration of about 40% to about 60% and a mixture of one or more unsaturated phospholipid, DMPC [14:0] having a carbon length of 14 and no unsaturated bonds, 1,2-dipalmitoyl-sn-glycero-3-phosphocholine (DPPC) [16:0], 1,2-distearoyl-sn-glycero-3-phosphocholine (DSPC) [18:0], 1,2-dioleoyl-sn-glycero-3-phosphocholine (DOPC) [18:1 (Δ9-Cis)], POPC [16:0-18:1], and DOTAP [18:1] at a molar concentration (in combination) of about 40% to about 60% of the lipid bilayer.

In certain embodiments, the lipid bilayer is comprised of one or more compositions selected from the group consisting of a phospholipid, a phosphatidyl-choline, a phosphatidyl-serine, a phosphatidyl-diethanolamine, a phosphatidylinosite, a sphingolipid, and an ethoxylated sterol, or mixtures thereof. In illustrative examples of such embodiments, the phospholipid can be a lecithin; the phosphatidylinosite can be derived from soy, rape, cotton seed, egg and mixtures thereof; the sphingolipid can be ceramide, a cerebroside, a sphingosine, and a sphingomyelin, and a mixture thereof; the ethoxylated sterol can be phytosterol, PEG-(polyethylene glycol)-5-soy bean sterol, and PEG-(polyethylene glycol)-5 rapeseed sterol. In certain embodiments, the phytosterol comprises a mixture of at least two of the following compositions: sitosterol, campesterol and stigmasterol.

In still other illustrative embodiments, the lipid bilayer is comprised of one or more phosphatidyl groups selected from the group consisting of phosphatidyl-choline, phosphatidyl-ethanolamine, phosphatidyl-serine, phosphatidyl-inositol, lyso-phosphatidyl-choline, lyso-phosphatidyl-ethanolamnine, lyso-phosphatidyl-inositol and lyso-phosphatidyl-inositol.

In still other illustrative embodiments, the lipid bilayer is comprised of phospholipid selected from a monoacyl or diacylphosphoglyceride.

In still other illustrative embodiments, the lipid bilayer is comprised of one or more phosphoinositides selected from the group consisting of phosphatidyl-inositol-3-phosphate (PI-3-P), phosphatidyl-inositol-4-phosphate (PI-4-P), phosphatidyl-inositol-5-phosphate (PI-5-P), phosphatidyl-inositol-3,4-diphosphate (PI-3,4-P2), phosphatidyl-inositol-3,5-diphosphate (PI-3,5-P2), phosphatidyl-inositol-4,5-diphosphate (PI-4,5-P2), phosphatidyl-inositol-3,4,5-triphosphate (PI-3,4,5-P3), lysophosphatidyl-inositol-3-phosphate (LPI-3-P), lysophosphatidyl-inositol-4-phosphate (LPI-4-P), lysophosphatidyl-inositol-5-phosphate (LPI-5-P), lysophosphatidyl-inositol-3,4-diphosphate (LPI-3,4-P2), lysophosphatidyl-inositol-3,5-diphosphate (LPI-3,5-P2), lysophosphatidyl-inositol-4,5-diphosphate (LPI-4,5-P2), and lysophosphatidyl-inositol-3,4,5-triphosphate (LPI-3,4,5-P3), and phosphatidyl-inositol (PI), and lysophosphatidyl-inositol (LPI).

In still other illustrative embodiments, the lipid bilayer is comprised of one or more phospholipids selected from the group consisting of PEG-poly(ethylene glycol)-derivatized distearoylphosphatidylethanolamine (PEG-DSPE), poly(ethylene glycol)-derivatized ceramides (PEG-CER), hydrogenated soy phosphatidylcholine (HSPC), egg phosphatidylcholine (EPC), phosphatidyl ethanolamine (PE), phosphatidyl glycerol (PG), phosphatidyl insitol (PI), monosialogangolioside, spingomyelin (SPM), distearoylphosphatidylcholine (DSPC), dimyristoylphosphatidylcholine (DMPC), and dimyristoylphosphatidylglycerol (DMPG).

In one illustrative embodiment of a nanocarrier of the invention:
(a) the one or more pharmaceutically-active agents include at least one anticancer agent;
(b) less than around 10% to around 20% of the anticancer agent is released from the porous nanoparticulates in the absence of a reactive oxygen species; and (c) upon disruption of the lipid bilayer as a result of contact with a reactive oxygen species, the porous nanoparticulates release an amount of anticancer agent that is approximately equal to around 60% to around 80%, or around 61% to around 79%, or around 62% to around 78%, or around 63% to around 77%, or around 64% to around 77%, or around 65% to around 76%, or around 66% to around 75%, or around 67% to around 74%, or around 68% to around 73%, or around 69% to around 72%, or around 70% to around 71%, or around 70% of the amount of anticancer agent that would have been released had the lipid bilayer been lysed with 5% (w/v) Triton X-100.

Nanocarriers of the invention can comprise a wide variety of pharmaceutically-active ingredients. Preferably, the active ingredients are anti-cancer agents selected from the group consisting of antimetabolites, inhibitors of topoisomerase I and II, alkylating agents, microtubule inhibitors, small molecule inhibitors, biotherapeutics and monoclonal antibodies, adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; dacarbazine; dactinomycin; actinomycin D; Darbepoetin alfa; daunorubicin, daunomycin; Denileukin diftitox, dexrazoxane; docetaxel; doxorubicin; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; valrubicin; valtorcitabine (monoval LDC); vinblastine; vinorelbine; zoledronate; and mixtures thereof.

More preferably, nanocarriers of the invention comprise an anti-cancer agent that is useful in the treatment of ovarian cancer or peritoneal cancers. Non-limiting examples of such anti-cancer drugs include doxorubicin, melphalan, bevacizumab, dactinomycin, cyclophosphamide, amifostine, etoposide, gemcitabine, altretamine, topotecan, cyclophosphamide, paclitaxel, carboplatin, cisplatin, and taxol.

Certain embodiments of the invention provide methods of treating a subject who suffers from a cancer in which a plurality of nanocarriers as described herein is intraperitoneally administered (e.g. by injection of a pharmaceutical formulation comprising a plurality of the nanocarriers and a pharmaceutically-acceptable diluent and/or excipient) to the peritoneum of a subject suffering from peritoneal cancer.

In certain embodiments of these methods of treatment:

(a) the nanocarrier comprises nanoparticulates that comprise one or more compositions selected from the group consisting of silica, a biodegradable polymer, a sol-gel, a metal and a metal oxide;
(b) subsequent to administration, the nanocarrier's lipid bilayer is disrupted upon contact with a reactive oxygen species (ROS) selected from the group consisting of ozone ($O_3$), hydrogen peroxide, hypochlorite ion, hydroxyl radical, superoxide anion ($O_2^-$), and peroxynitrite; and
(c) the nanocarrier's one or more pharmaceutically-active agents include an anti-cancer agent selected from the group consisting of doxorubicin, melphalan, bevacizumab, dactinomycin, cyclophosphamide, amifostine, etoposide, gemcitabine, altretamine, topotecan, cyclophosphamide, a taxane chemotherapeutic agent, e.g., paclitaxel/taxol or docetaxel, etc. or a platinum based chemotherapeutic agent, e.g., carboplatin, cisplatin, etc.

In illustrative formulations and methods described in the paragraph above, the nanocarrier can comprise a plurality of porous silica nanoparticulates that:

(a) are loaded with one or more pharmaceutically-active agents preferably selected from the group consisting of doxorubicin, melphalan, bevacizumab, dactinomycin, cyclophosphamide, amifostine, etoposide, gemcitabine, altretamine, topotecan, cyclophosphamide, a taxane chemotherapeutic agent, e.g. paclitaxel/taxol or doxetaxel, or a platinum based chemotherapeutic agents such as carboplatin, cisplatin or oxalaplatin; and
(b) that are encapsulated by and that support a lipid bilayer comprised of one or more compositions selected from the group consisting of a phospholipid, a phosphatidyl-choline, a phosphatidyl-serine, a phosphatidyl-diethanolamine, a phosphatidylinosite, a sphingolipid, and an ethoxylated sterol, or mixtures thereof;
wherein subsequent to administration, the nanocarrier's lipid bilayer is disrupted in vivo upon contact with a reactive oxygen species (ROS) selected from the group consisting of ozone ($O_3$), hydrogen peroxide, hypochlorite ion, hydroxyl radical, superoxide anion ($O_2^-$), and peroxynitrite.

In other embodiments of the methods of treatment of the invention, the subject is co-administered one or more additional anti-cancer agents or anti-cancer treatments (e.g. radiation) along with the nanocarrier composition. The additional anti-cancer agents or anti-cancer treatments and nanocarrier composition can be administered at different times or concomitantly to the subject. Certain embodiments entail intraperitoneally administering a pharmaceutical formulation comprising a plurality of the nanocarriers and a pharmaceutically-acceptable diluent and/or excipient to the peritoneum of a subject suffering from peritoneal cancer.

In still other embodiments, the invention provides a pharmaceutical composition comprising:

(a) an intraperitoneally-administered nanocarrier composition comprising a plurality of porous nanoparticulates that (1) are loaded with one or more pharmaceutically-active agents and (2) that are encapsulated by and that support a lipid bilayer which is disrupted in vivo upon contact with a reactive oxygen species; and
(b) at least one pharmaceutically acceptable diluent or pharmaceutically-acceptable excipient.

In one example of a pharmaceutical composition of the invention:

(a) the nanocarrier composition comprises nanoparticulates that comprise one or more compositions selected from the group consisting of silica, a biodegradable polymer, a sol-gel, a metal and a metal oxide;

(b) the lipid bilayer of the nanoparticulates is disrupted in vivo upon contact with a reactive oxygen species (ROS) selected from the group consisting of ozone ($O_3$), hydrogen peroxide, hypochlorite ion, hydroxyl radical, superoxide anion ($O_2^-$), and peroxynitrite; and (c) the one or more pharmaceutically-active agents include an anti-cancer agent selected from the group consisting of doxorubicin, melphalan, bevacizumab, dactinomycin, cyclophosphamide, amifostine, etoposide, gemcitabine, altretamine, topotecan, cyclophosphamide, a taxane chemotherapeutic agent, e.g. paclitaxel/taxol or doxetaxel, or a platinum based chemotherapeutic agents such as carboplatin, cisplatin or oxalaplatin.

The term "patient" or "subject" is used throughout the specification to describe an animal, preferably a human, to whom treatment, including prophylactic treatment, with the compositions according to the present invention is provided. For treatment of those infections, conditions or disease states which are specific for a specific animal such as a human patient, the term patient refers to that specific animal.

The term "effective amount" is used throughout the specification to describe concentrations or amounts of formulations or other components which are used in amounts, within the context of their use, to produce an intended effect according to the present invention. The formulations or component may be used to produce a favorable change in a disease or condition treated, whether that change is a remission, a favorable physiological result, a reversal or attenuation of a disease state or condition treated, the prevention or the reduction in the likelihood of a condition or disease-state occurring, depending upon the disease or condition treated. Where formulations are used in combination, each of the formulations is used in an effective amount, wherein an effective amount may include a synergistic amount. The amount of formulation used in the present invention may vary according to the nature of the formulation, the age and weight of the patient and numerous other factors which may influence the bioavailability and pharmacokinetics of the formulation, the amount of formulation which is administered to a patient generally ranges from about 0.001 mg/kg to about 50 mg/kg or more, about 0.5 mg/kg to about 25 mg/kg, about 0.1 to about 15 mg/kg, about 1 mg to about 10 mg/kg per day and otherwise described herein. The person of ordinary skill may easily recognize variations in dosage schedules or amounts to be made during the course of therapy.

The term "prophylactic" is used to describe the use of a formulation described herein which reduces the likelihood of an occurrence of a condition or disease state in a patient or subject. The term "reducing the likelihood" refers to the fact that in a given population of patients, the present invention may be used to reduce the likelihood of an occurrence, recurrence or metastasis of disease in one or more patients within that population of all patients, rather than prevent, in all patients, the occurrence, recurrence or metastasis of a disease state.

The term "pharmaceutically acceptable" means that a nanocarrier as described herein, or component thereof or a formulation comprised of such a nanocarrier, or an additive, diluent or excipient of a formulation as described herein, is not unacceptably toxic to the subject to which it is administered.

The term "taxanes" or "taxane chemotherapeutic agents" include, but are not limited to, paclitaxel (Taxol®), docetaxel (Taxoterel®), taxane derivatives such as IDN 5390, GRN1005, the taxane derivatives described in EP 2330100A1, and the taxane derivatives described or referenced in *Bioscience, Biotechnology, and Biochemistry*, Vol. 76 (2012), No. 2 pp. 349-352. Preferred taxanes include paclitaxel and docetaxel.

The term "platinum based chemotherapeutic agent" is used to describe a chemotherapeutic agent which contains platinum. Preferred platinum based chemotherapeutic agents include cisplatin, oxalaplatin and carboplatin.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascetic and solid tumors.

Examples of cancers which may be treated using various embodiments according to the present invention include, without limitation, carcinomas (e.g., squamous-cell carcinomas, basal cell carcinomas adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; benign and malignant lymphomas, particularly Burkitt's lymphoma and Non-Hodgkin's lymphoma, benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal, sarcomas, neurofibromas, and Schwannomas); germ-line and non-germ line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991). It is noted that in the case of peritoneal cancers, the preferred route of administration is intraperitoneal (IP administration). In the case of cancers which are non-peritoneal cancers, the preferred route of administration of compositions according to the present invention is directly into the cancer/tumor.

The term "peritoneal cancer" refers to a somewhat rare cancer that develops in the thin layer of tissue that lines the abdomen called the peritoneum. It also covers the uterus, bladder, and rectum. Peritoneal cancer is sometimes confused with intestinal or stomach cancer. Peritoneal cancer is not that the same as those cancers that metastasize to the peritoneum, inasmuch as peritoneal cancer starts in the peritoneum. As such, it is generally referred to as primary peritoneal cancer. Primary peritoneal cancer (PPC, or PPCa)

is a cancer of the cells lining the peritonium, or abdominal cavity. Peritoneal cancer acts and looks like ovarian cancer. This is mainly because the surface of the ovaries is made of epithelial cells, as is the peritoneum. Primary peritoneal cancer or carcinoma is also known as: serous surface papillary carcinoma, primary peritoneal carcinoma, extra-ovarian serous carcinoma, primary serous papillary carcinoma, psammomacarcinoma.

Formulations according to the present invention may be co-administered with additional anticancer agents. These agents include, for example, antimetabolites, inhibitors of topoisomerase I and II, alkylating agents, microtubule inhibitors (e.g., taxol), small molecule inhibitors, biotherapeutic agents and monoclonal antibodies. Specific anticancer co-therapies for use in the present invention include, for example, adriamycin aldesleukin; alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; dacarbazine; dactinomycin; actinomycin D; Darbepoetin alfa; daunorubicin, daunomycin; Denileukin diftitox, dexrazoxane; docetaxel; doxorubicin; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemcitabine, gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); uracil mustard; vairubicin; valtorcitabine (monoval LDC); vinblastine; vinorelbine; zoledronate; and mixtures thereof, among others.

Formulations of the invention may include a pharmaceutically acceptable diluent, carrier, solubilizer, emulsifier, preservative and/or adjuvant. Acceptable formulation materials preferably are nontoxic to recipients at the dosages and concentrations employed. The pharmaceutical formulations may contain materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counter ions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18.sup.th Edition, (A. R. Gennaro, ed.), 1990, Mack Publishing.

Primary vehicles or carriers in a pharmaceutical formulation can include, but are not limited to, water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical formulations can comprise Tris buffer of about pH 7.0-8.5, or acetate buffer of about pH 4.0-5.5, which may further include sorbitol or a suitable substitute. Pharmaceutical formulations of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the formulations may be formulated as a lyophilizate using appropriate excipients such as sucrose. Formulation components are present in concentrations that are acceptable to the site of administration. Buffers are advantageously used to maintain the composition at physiological pH or at a slightly lower pH, typically within a pH range of from about 5 to about 8.

The therapeutic formulations for use in this invention may be in the form of a pyrogen-free, parenterally acceptable aqueous solution. Preparation involves the formulation of the desired nanocarrier, which may provide controlled or sustained release of the product which may then be delivered via a depot injection. Formulation with hyaluronic acid has the effect of promoting sustained duration in the circulation.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the formulation of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

These and other aspects of the invention are described further in the following non-limiting examples.

EXAMPLE 1

Generation of Ozone and Disruption of SLB.
1. Overview.

Figure 3:
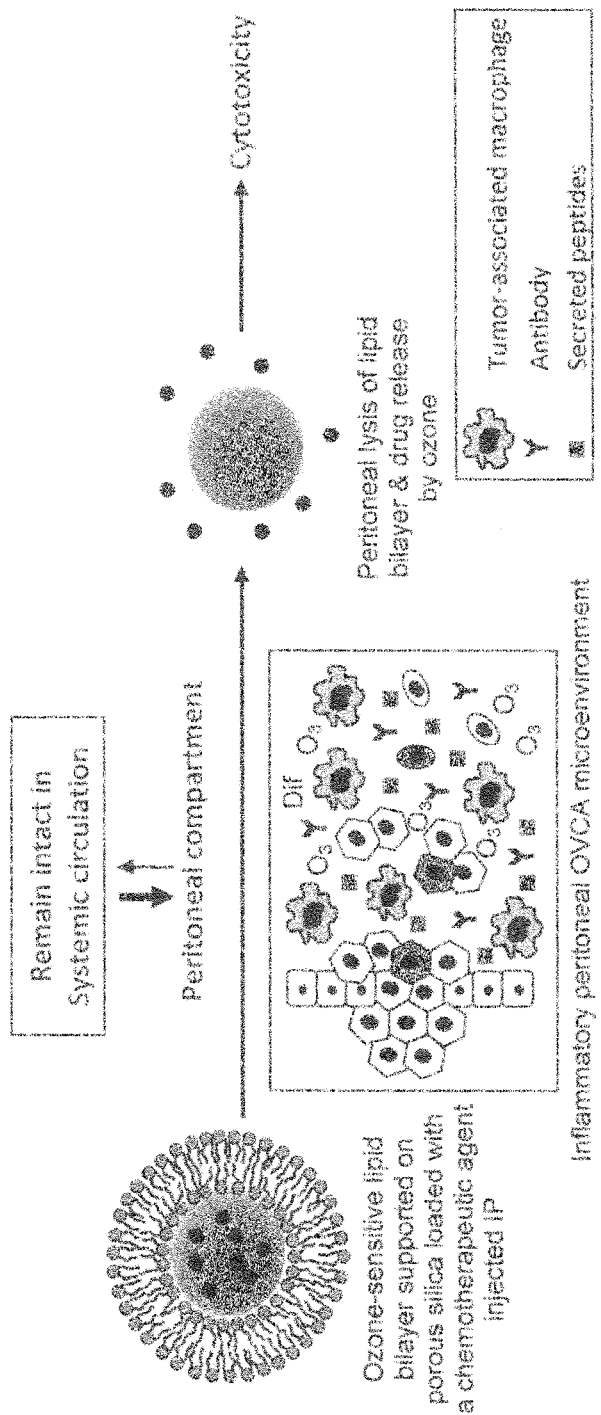
FIG. 3. Significance of using an ROS-sensitive nanocarrier for OVCA therapy is that it will exclusively release its content in the inflammatory peritoneal OVCA microenvironment but not in the systemic circulation. This will enhance IP therapy of targeting several types of OVCA drug-resistant cells (SCs, MCAs, CSCs) while reducing systemic toxicity.

Since OVCA is a peritoneal disease, then, logically, introducing therapeutic drugs intraperitoneally (IP) directly to the site of the disease must have higher efficacy than the intravenous (IV) route. In addition, pre-clinical studies demonstrate that the IP route allows for administering higher concentration of chemotherapeutic agents than the IV route [45]. In fact, the IP route of administering chemotherapy conferred greater overall survival rates alone or in combination with IV route [2-5]; however, the main problem associated with IP administration is higher rates of systemic toxicities [2, 35, 46]. We plan to design a nanocarrier that releases its therapeutic content only peritoneally and not in the circulation in order to overcome the current problems of systemic toxicity associated with IP therapy. Our nanocarrier will be made of an ROS-sensitive lipid bilayer that is supported on porous silica nanospheres (FIG. 3). The significance of being ROS-sensitive is that its therapeutic content can be released exclusively within the inflammatory peritoneal microenvironment of the OVCA that is rich with activated immune cells that will cause lysis of the lipid bilayer. At the same time having the lipid bilayer supported on silica spheres will stabilize them when facing lower ROS concentrations upon entrance into the circulation through the peritoneal cavity. The lower and controlled ROS levels within the blood is due to antioxidants that inhibit the effect of ROS in the circulation including preventing its bacterial toxicity [47, 48].

The majority of nanocarriers will be localized peritoneally (FIG. 3), thus preventing significant drug release at inflammatory sites other than the targeted site. The significance of IP administration of drugs is that it treats local and disseminated disease along with SCs, MCAs and CSCs as the OVCA metastasis is largely confined to the peritoneum (FIG. 1). Targeting these cells directly peritoneally is important as persistence of these cells is a known contributor to therapy resistance and relapse in treatment [6-12]. Thus this mode of therapy should overcome chemotherapeutic resistance of OVCA, and the significance of our nanotechnology platform in particular is that it will reduce systemic toxicity.

Figure 4:
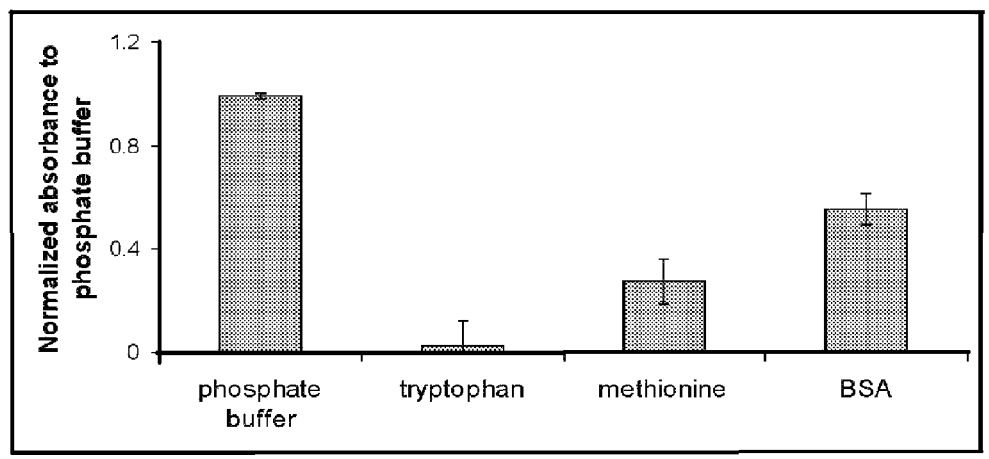
FIG. 4. Ozone production catalyzed by amino acids in cell-free system in presence of 10 μM 6-biopterin and with UVA irradiation. Tubes also contained 30 μM indigo carmine which got converted by ozone to isatin sulfonic acid as detected by a decrease in absorbance at 610 nm. 1 mM of each amino acid and 5 mg/mL BSA in phosphate buffer were tested. Error bars represent standard deviation for three replicates.

Thus, upon administration nanocarriers of the invention: (1) ROS is generated from singlet oxygen species as mediated by activated immune cells in inflammatory diseases like OVCA; (2) ROS damages and causes lysis of lipid bilayers; and (3) robust supported lipid bilayer membrane assemblies can be easily formed on porous silica with capabilities of entrapping chemotherapeutic agents [27-29].
2. Approach.
Preliminary Studies Supporting Aims:

We successfully generated ozone (a molecule with the chemical signature of ozone) in a cell-free system by employing a photochemical source i.e. by adding a photosensitizer and exposing the tube contents to UVA irradiation. Our findings are summarized in this section. Four amino acids (tryptophan, methionine, cysteine, and histidine), but not other amino acids were reported to have the same catalytic activity as antibodies needed for water oxidation to produce ozone along with increasing bactericidal activity of neutrophils by employing a photochemical source [49]. For our preliminary studies we used amino acids as the simplest mechanism to generate ozone. The photosensitizer we used is 6-biopterin (Sigma-Aldrich, St Louis, Mo.) [49], and the UVA irradiation (315-400 nm) was provided by an ozone-free 1000W Xenon arc lamp as a solar simulator with blocking UVB radiation by appropriate filters (Oriel Instruments, Stratford, Conn.). The output of UVA radiation was confirmed and was measured by a UV meter (Model 3D, Solar Light, Glenside, Pa.) to be 6 mW/cm$^2$; we exposed the samples for 4 minutes. Ozone was detected through its conversion of indigo carmine (a blue dye with absorbance maximum at 610 nm) to isatin sulfonic acid (colorless) as we monitored this conversion by measuring absorbance at 610 nm as previously described [16, 49]. FIG. 4 shows that we photochemically generated ozone in a reaction catalyzed by tryptophan and to a lower extent by methionine, which is consistent with a previous report [49], while bovine serum albumin (BSA) only slightly generated ozone while phosphate buffer could serve as a negative control as previously reported [49].

Figure 5:
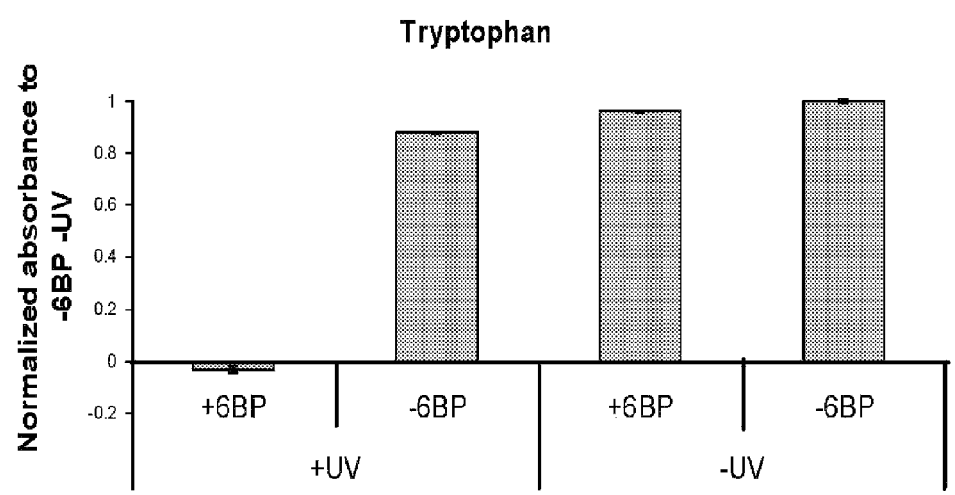
FIG. 5. Both UVA and 6BP are required to generate ozone by tryptophan. 1 mM Trp was tested. Error bars represent standard deviation for three replicates.
Figure 6:
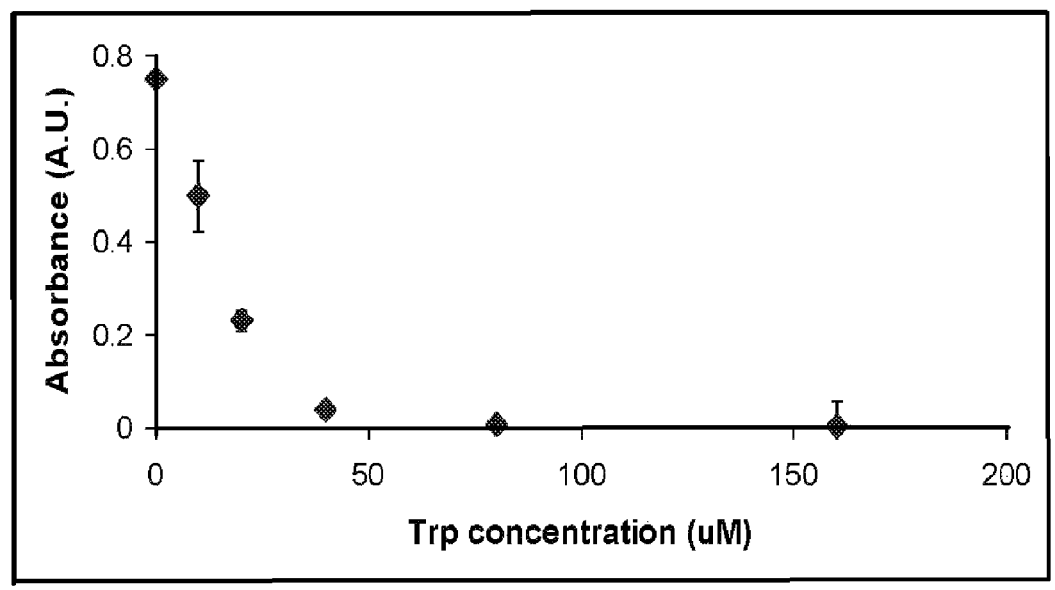
FIG. 6. Dose response curve for generation of ozone by increasing concentrations of Trp. Tested concentrations were 0, 10, 20, 40, 80 & 160, 500, 1000 μM tryptophan. Higher concentrations 500 μM and 1 mM Trp are not shown as they gave similar results to 160 μM. Error bars represent standard deviation for three replicates.
Figure 7:
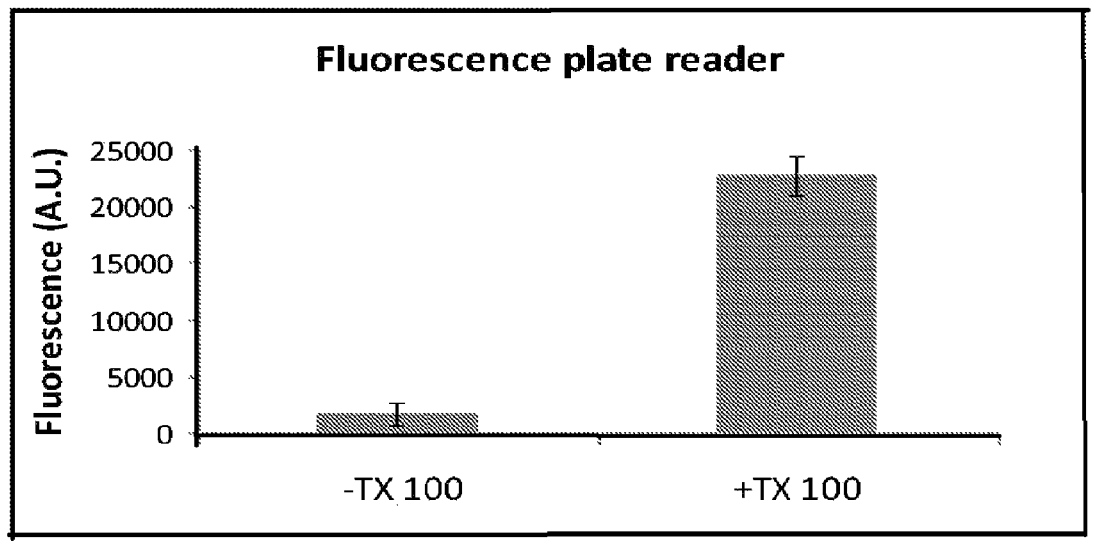
FIG. 7. Disruption of lipid bilayer by Triton X-100. 3 μm silica spheres with 50 Å nominal pore size were incubated with 5 mM fluorescein then coated with a lipid bilayer made of egg phosphatidyl choline. Part of spheres was left with no treatment, and part was treated with Triton X-100 (TX 100) at a final concentration of 5% (w/v). Fluorescence of the supernatant after sedimenting the spheres was examined to check for release of fluorescein.

Since Tryptophan (Trp) generated the highest level of ozone we continued using it in the next experiments and we used both phosphate buffer and BSA as negative controls. FIG. 5 demonstrates that tryptophan alone is not capable of water oxidation, but both presence of 6-biopterin (6BP) as the photosensitizer along with the exposure to UVA are required for this reaction, as their presence has been reported to generate the needed singlet oxygen as a substrate in addition to water for this reaction [16, 49]. Furthermore, tryptophan converted singlet oxygen to ozone in a dose-dependent manner (FIG. 6). All these experiments demonstrate our success in generating ozone (a molecule with the chemical signature of ozone) by the amino acid tryptophan in a cell-free and a sphere-free system. The platform we plan to use employs supported lipid bilayers (SLBs) on porous silica. We will test the disruption of SLBs by ozone employing the above described system to generate ozone photochemically by Trp. For detecting disruption of the SLB we tested the proof-of-concept by adding Triton X-100 (TX 100) to spheres encapsulating fluorescein within 3 microns porous silica (Macherey-Nagel, Germany) followed by forming the SLB as previously described [27] (FIG. 7). Disruption of the SLB by TX 100 caused release of the encapsulated fluorescein (14 fold increase in fluorescence by TX100 vs. untreated spheres). This was done to demonstrate that we are capable of detecting SLB disruption and release of contents of the porous spheres by employing a fluorescent dye.

In summary, our preliminary data show that we were successful in producing ozone photochemically by amino acids and that we have a system for detecting lysis of SLBs and release of their encapsulated contents.

EXAMPLE 2

Porous Silica Spheres.

Figure 8:
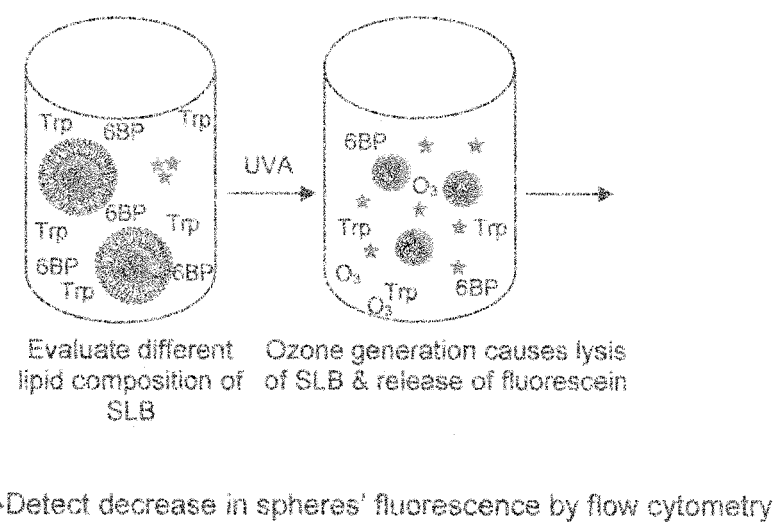
FIG. 8. Approach for aim 1 involves optimizing the SLB lipid composition to select maximum lysis by ozone that is generated photochemically by Trp in a tube. Lysis of SLB by ozone will release entrapped fluorescein (green stars) and this decrease in the fluorescence of silica will be detected by flow cytometry.

The system described under FIG. 7 is exposed to ozone produced photochemically (i.e. by exposure to UVA and presence of 6BP) by tryptophan. Porous nanosilica spheres with size range 200-500 nm are synthesized according to published procedure [50]. Flow cytometry detects release of the fluorescein content of the nanocarrier (FIG. 8). To optimize the lipid make up of the SLB, various phosphatidyl-cholines (PCs) are evaluated in addition to cholesterol (all available from Avanti Polar Lipids, Alabaster, Ala.). PCs tested include egg PC as an example of a lipid mixture that has ~54% of its content as unsaturated PC. Additional PCs evaluated have different chain lengths and varying saturations to optimize the lysis in response to ozone generation while maintaining stability on silica. Some PCs that are used are reported to undergo lysis by ozone generation when they are part of SLBs include 1,2-dimyristoyl-sn-glycero-3-phosphocholine (DMPC), 1,2-dioleoyl-3-trimethylammonium-propane (DOTAP) and 1-palmitoyl-2-oleoyl-sn-glycero-3-phosphocholine (POPC) [23, 24]. Egg PC has a low transition temperature ($T_m$) and thus it maintains its fluid phase at room temperature, which makes it easy to use at room temperature for generating SLBs on nanospheres.

Mix with the egg PC other PCs of varying length and saturations as listed above, with adjusting the temperature under which they are prepared based on their $T_m$. These PCs include DMPC [14:0] (i.e. carbon length=14 with zero unsaturated bonds), 1,2-dipalmitoyl-sn-glycero-3-phosphocholine (DPPC) [16:0], 1,2-distearoyl-sn-glycero-3-phosphocholine (DSPC) [18:0], 1,2-dioleoyl-sn-glycero-3-phosphocholine (DOPC) [18:1 (Δ9-Cis)], POPC [16:0-18:1], and DOTAP [18:1]. Test mixtures of each of these lipids with egg PC at 10, 20, and 40 mole % of PC content. Before testing the response of these SLBs to ozone that is produced photochemically by tryptophan, confirm the stability of the SLBs on nanosilica by examining leakage of fluorescein over time as detected by flow cytometry. Any unstable PCs are excluded from further experimentation.

Carry out ozone lysis experiments with the stable PC mixtures supported on porous silica nanospheres that encapsulate fluorescein as ozone will be produced photochemically by tryptophan and the release of fluorescein will be detected by flow cytometry. All samples are compared to the positive control of SLB disruption by 5% (w/v) TX 100. Negative controls include (1) same samples without exposure to UV; and (2) same samples without presence of 6BP. Other negative controls have only buffer or BSA instead of tryptophan. Select the best PC mixture that provides stability in absence of ozone, but undergoes maximum lysis in presence of ozone. Maximum lysis is defined as lysis releasing ~70% of fluorescent content when compared to lysis by TX 100 (which will be considered as 100% lysis). The rational for this is that in our experience TX 100 results in the highest lysis of lipid bilayers, whereas biological molecules usually result in reduced lysis, for example melittin (a membrane active peptide) causes 70-80% lysis (relative to TX 100) [27, 51].

After selecting the best mixture, test the effect of incorporating cholesterol into that PC mixture at 5, 10, and 20 mole % of lipid content, to evaluate whether this will enhance lysis in presence of ozone or have the opposite effect (i.e. stabilizing). For all experiments, data is collected in triplicates and comparisons will be done using a non-parametric Welch's two sample t-test where any p-value below 0.05 will be considered statistically significant.

Determine the optimal amount of fluorescein trapped into spheres to be detectable by flow cytometry without causing self-quenching [50]. If necessary, generate ozone using a corona discharge ozonizer which has an integrated redox controller to control the amount of ozone generated and has a redox potential electrode to measure the output.

EXAMPLE 3

Cytotoxicity of DOX in the Presence of ROS.

One of the observed improvements in OVCA therapy results from using nanocarriers leading to enhanced targeting of OVCA and the use of chemotherapeutic agents other than platinum- and taxane-based therapies (to which OVCA may become resistant). For example, use of doxorubicin-loaded liposomes that are functionalized by polyethylene glycol (PEG) for OVCA such as Caelyx® (Schering-Plough) and Doxil® (Centocor Ortho Biotech) [5, 52-54]. These nanocarriers demonstrated the efficacy of using doxorubicin (DOX) in OVCA, although DOX was not among the chemotherapeutic agents usually employed for OVCA therapy. Because of that we also plan to test DOX with our system in addition to the advantage of the fluorescent nature of DOX, which allows for easy detection intracellularly using fluorescence microscopy. Aim 2 tests the cytotoxicity of DOX released by the vehicle we are developing in this proposal in presence of ROS. For that reason, we will test this DOX-loaded nanocarrier with cultured OVCA cells. The ozone will be generated by co-culturing OVCA cells with macrophages that will be activated by addition of phorbol myristate acetate (PMA) [15-17, 43, 49]. This system will be evaluated because it simulates the in vivo inflammatory environment of OVCA.

A modification of Boyden Chamber assay will be employed [55] as we will culture OVCA cells (cells to be tested include OVCA 433, OVCA 429, and SKOV-3ip) as monolayers on membranes of inserts for 24-well plates, whereas macrophages (peritoneal macrophage cell line H36.12j) will be co-cultured as a cell suspension in the wells into which the inserts are placed. The nanocarriers will be added to the inserts and the macrophages will be activated by adding PMA as previously described [15-17, 43, 49]. After 24 hr incubation, cells on membranes of the inserts will be fixed and the nuclei of cells on membranes will be stained by DAPI followed by mounting on a slide to be examined by fluorescence microscopy. In addition to visualizing nuclei, cellular uptake of DOX can be detected in cells that took it up but are not dead yet through its fluorescence (excitation 480 nm, emission 550 nm). The number of nuclei reflects the number of live cells, so toxicity to cells means reduced number of nuclei.

For all above experiments, DOX will be added directly to cells as a positive control after determining the optimal concentration of the drug to be used to cause at least 70% cytotoxicity. We have data showing 96% cell death with DOX at final concentration of 1 μM after 72 hr incubation (refer to QUANTITATIVE MILESTONES below). Negative controls include (1) absence of ROS either by not activating macrophages; and (2) addition of nanocarriers devoid of DOX but with generation of ROS. Data will be collected in triplicates and comparisons will be done using a non-parametric Welch's two sample t-test where any p-value below 0.05 will be considered statistically significant. All the experiments described above are essential for the purpose of establishing the proof-of-concept of ability of the developed nanocarriers to release in vitro their cytotoxic therapeutic content to OVCA cells in presence of a system the simulates in vivo inflammation and generation of ROS.

In this aim we will establish the proof-of-concept for release of chemotherapeutic agents in vitro to cells from the nanocarriers developed in this proposal in presence of activated macrophages that generate ROS. For this proof of concept, microspheres, not nanospheres are used in vitro). We expect that ROS that is capable of lysing lipid bilayers will cause release of cytotoxic DOX to OVCA cells leading to their death. The only potential problem for this aim is that activated macrophages may not be sufficient to generate ROS because the in vivo OVCA microenvironment is rich with antibodies including auto antibodies [57-59] and many peptides that contribute to the inflammatory environment and generation of ROS. If that is the case, we will add the amino acid tryptophan besides activating the macrophages to generate ROS in culture to test the effect on releasing DOX.

EXAMPLE 4

Quantitative Milestones:

Select the best PC mixture that provides stability in absence of ROS, but undergoes maximum lysis in presence of ROS. Maximum stability in absence of ROS is defined as <15% leakage of fluorescein, while maximum lysis is defined as lysis releasing ~70% of fluorescent content when compared to lysis by 5% (w/v) TX 100 (which will be considered as 100% lysis). The rational for this is that in our experience TX 100 results in the highest lysis of lipid bilayers, whereas biological molecules usually result in reduced lysis, for example melittin (a membrane active peptide) ranges between 70-80% lysis (relative to TX 100) [27, 51].

Demonstrate in the experiment of Example 3 that our platform will cause at least 70% cytotoxicity after 24 hr incubation. In our experience, treatment with 1 µM DOX alone causes ~45% cytotoxicity after 24 hr incubation, and ~96% cytotoxicity after 72 hr incubation (data not shown). However, for the nanocarriers, 72 hr may allow internalization of the nanocarriers and release of DOX regardless of presence of ROS. For that reason we are selecting the 24 hr incubation as the effect by that time will be due to ROS only and we expect it to result in ~70% toxicity. If we are successful in vitro, then this provides proof-of-principle for a future R33 application where this platform can be tested in vivo in peritoneal cancer mouse model of OVCA.

Results.

Testing in-vitro Disruption of Lipid Bilayers by Ozone and Reactive Oxygen Species Generated by Activated Macrophages:

Cells:

H36.12j and RAW264.7 macrophages cell line was obtained from American Type Cell Culture (ATCC, Manassas, Va.). H36.12j cells were grown in Delbecco's Modified Eagles Medium (ATTC, Manassas, Va.) supplemented with 10% (v/v) Heat-inactivated iron bovine calf serum. Propagation was at 37° C. in 5% carbon dioxide. RAW264.7 cells were grown in Delbecco's Modified Eagles Medium (ATTC, Manassas, Va.) supplemented with 10% (v/v) fetal bovine serum. Propagation was at 37° C. in 10% carbon dioxide.

Figure 9:
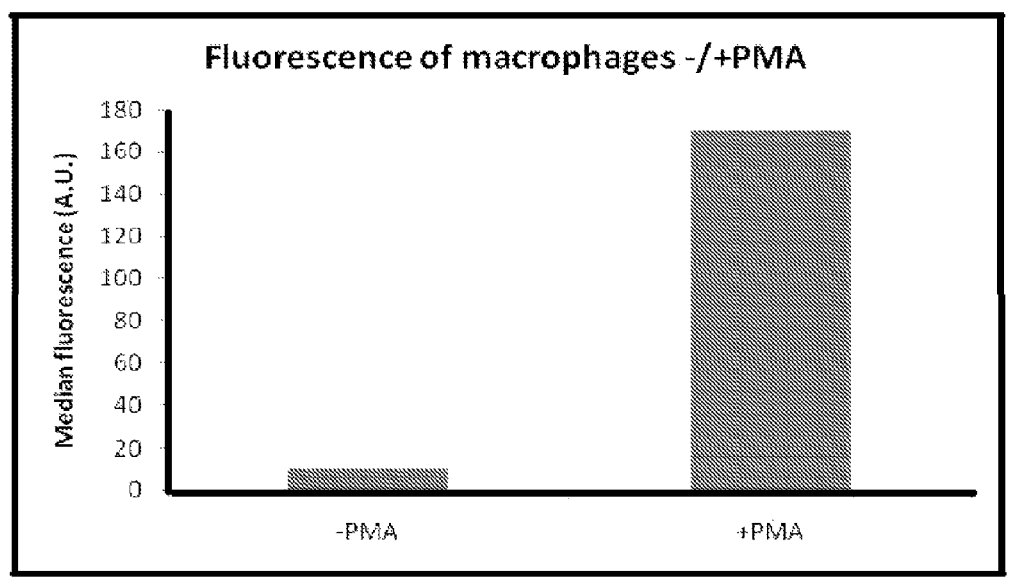
FIG. 9. Detection of ROS using a fluorescent dye upon activation of macrophages with phorbol myristate acetate (PMA)

Confirming Generation of ROS by Activated Macrophages:

Cells ($0.2 \times 10^6$ in 500 uL media) were pipetted into each well of 24-well plate. Cells were stimulated with phorbol-12-myristate-13-acetate (PMA), (Sigma—Saint Louis, Mo.) at a final concentration of 1 µM for 30 minutes, followed by an incubation with 5 µM CellROX (Invitrogen) for 30 minutes to detect ROS. Fluorescence was then determined by flow cytometry. Results demonstrated that ROS was generated by macrophages upon activation with PMA (FIG. 9).

Figure 10:
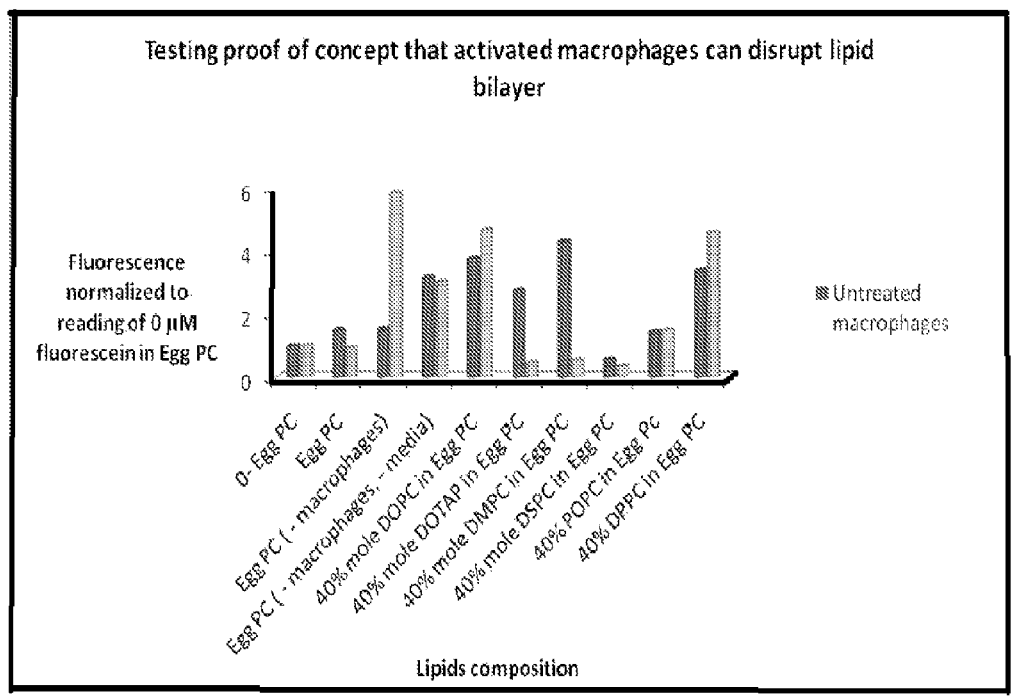
FIG. 10. Macrophage disruption of various lipid bilayers upon activation with PMA.

Testing Disruption of Lipids by Activated Macrophages:

Cells ($1 \times 10^5$ in 500 uL media) were pipetted into each well of 24-well plate. Tryptophan in PBS was added to each well at a final concentration of 1 mM. Then, microspheres coated with lipids and encapsulating fluorescein were added to the wells. Lastly, phorbol-12-myristate-13-acetate (PMA), (Sigma—Saint Louis, Mo.) at a final concentration of 50 ng/ml or DMSO control (Sigma-Saint Louis, Mo.) were added to the wells. The cells were incubated for 1 hour and the supernatants were collected to check the microspheres' fluorescence using the flow cytometer. Lipids tested were 40-mole % DOPC in egg-PC; 40-mole % DOTAP in egg-PC, 40-mole % DMPC in egg-PC, 40-mole % DSPC in egg-PC, and 40-mole % DPPC in egg-PC. Controls included spheres without cells and spheres with PBS instead on media. FIG. 10 shows upon activation of macrophages with PMA to generate reactive oxygen species that there was a significant disruption of supported lipid bilayers as detected by reduction in fluorescence with two lipid compositions: 40 mole % DOTAP in egg PC and 40 mole % DMPC in egg PC.

Figure 11:
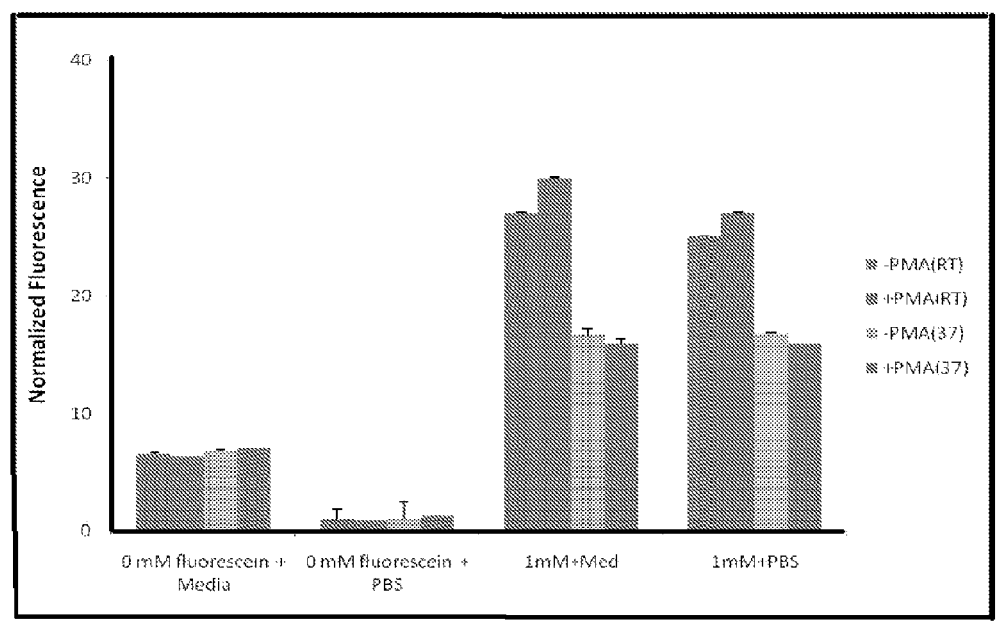
FIG. 11. In absence of macrophages, negligible increase in fluorescence in presence of media, which is a direct result of presence of phenol red in the media; the following conditions applied: (1) nanocarriers in phosphate buffered saline (PBS) versus media, (2) incubation at room temperature (RT) versus 37° C., and (3) in presence and in absence of PMA.

Evaluating Effect of Media, Temperature and PMS on Lipid Bilayers Made of Egg-PC:

We evaluated if adding PMA and incubating cells at 37° C. had an affect on the egg-PC lipid bilayer in absence of macrophages. For that reason we repeated the experiments carried out for FIG. 10 with the exception of not adding any macrophages. We did these experiments with nanocarriers with evaluating the following conditions: (1) nanocarriers in phosphate buffered saline (PBS) versus media, (2) incubation at room temperature (RT) versus 37° C., and (3) in presence and in absence of PMA. FIG. 11 shows the results for these experiments demonstrating negligible increase in fluorescence in presence of media, which is a direct result of presence of phenol red in the media. Since the increase is negligible and since presence of media would be a constant in our experiments with cells as it will be present in every sample, so this minimal increase can be ignored. Presence of PMA had no effect on the nanocarriers. Increasing the temperature had a significant decrease in fluorescence which is expected with egg-PC and needs to be evaluated with other lipids.

Knockdown of Folate Reptor α (FRα) in Ovarian Cancer Cells:

Our aim was to select for experimentation an ovarian cancer cell line that expresses high levels of FRα, while using as a negative control a cell line that does not express FRα. The ovarian cancer cell lines that were examined by RT-PCR included OVCA 432, OVCA 420, SKOV-3, DOV13, OVCA 433, OVCA 429, and OVEA6. FIG. 12 shows FRα-overexpressing candidates: SKOV-3 and OVCA432. High levels of FRα were previously reported in OVCA 432, and SKOV-3, whereas the other cell lines evaluated here were not studied previously. We will use SKOV-3 cells as a positive cell lines for FRα for future experiments.

Figure 13:
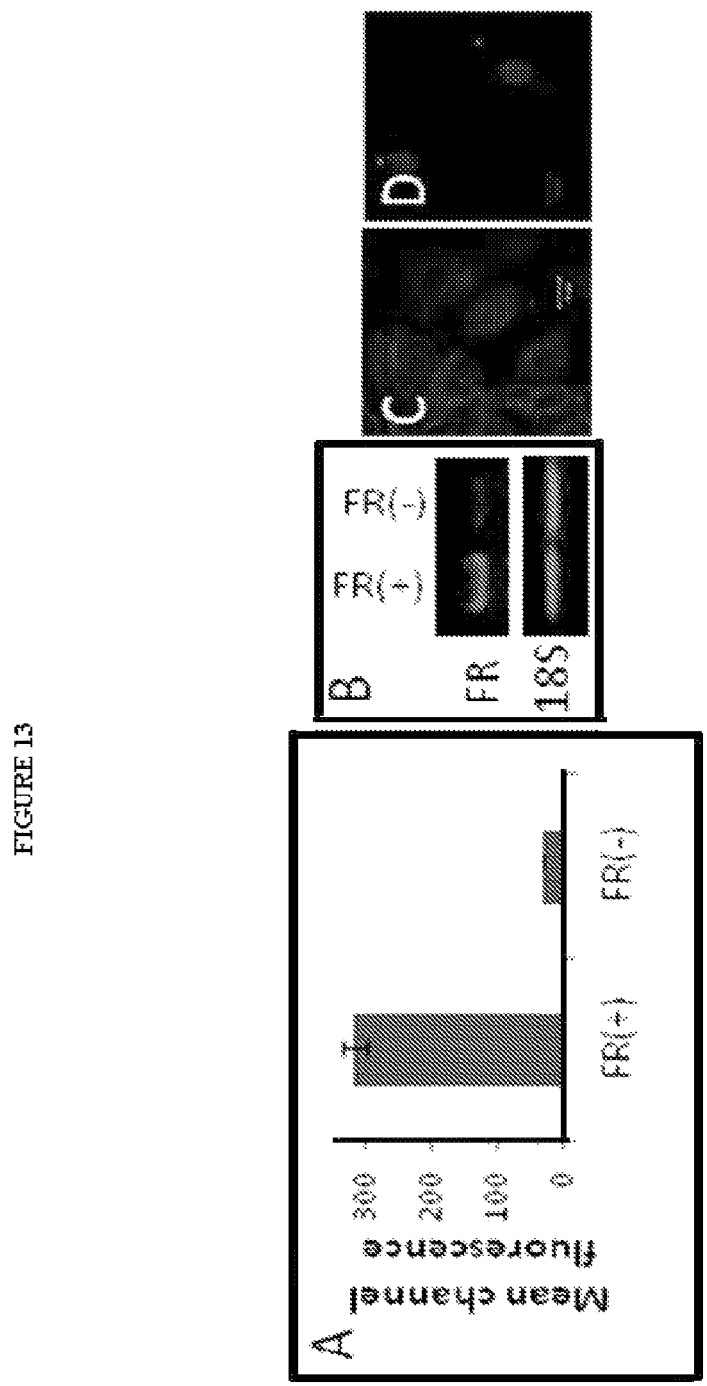
FIG. 13. Confirming knock down of FRα and specific uptake of folic acid-functionalized nanocarrierss by FR(+) cells but not FR(−) cells. (A) Flow cytometry showing protein level of FRα. (B) RT-PCR for FRα in parental cell line SKOV-3 (FR(+)) and cells with knocked-down expression of FRα (FR(−)) with 18S as internal control. (C,D) Confocal microscopy images for FR(+) cells (left) and FR(−) cells (right) demonstrating specific uptake of nanocarriers functionalized with folic acid by FR(+) cells but not FR(−) cells. The scale bar=20 μm.

We knocked down the expression of FRα in SKOV-3 cells using RNAi (Origene, Rockville, Md.) and found that this eliminated the uptake of folate-PEG-functionalized nanocarriers, which demonstrates the specificity of the uptake of these nanocarriers through FRα (FIG. 13).

REFERENCES

1. Scully, R., R. Young, and P. Clement, *Tumors of the ovary, maldeveloped gonads, allopian tube, and broad ligament*. Atlas of Tumor Pathology, ed. J. Rosia and L. Sobin. Vol. Fascicle 23. 1998, Washington D.C.: Armed Forces Institute of Pathlogy.
2. Metzger-Filho, O., C. Moulin, and V. D'Hondt, *First-line systemic treatment of ovarian cancer: a critical review of available evidence and expectations for future directions*. Curr Opin Oncol, 2010. 22(5): p. 513-520.
3. Zeimet, A. G., et al., *Pros and cons of intraperitoneal chemotherapy in the treatment of epithelial ovarian cancer*. Anticancer Res, 2009. 29(7): p. 2803-8.

4. Markman, M. and J. L. Walker, *Intraperitoneal chemotherapy of ovarian cancer: a review, with a focus on practical aspects of treatment*. J Clin Oncol, 2006. 24(6): p. 988-994.
5. Liu, J. and U. A. Matulonis, *New advances in ovarian cancer*. Oncology (Williston Park), 2010. 24(8): p. 721-728.
6. Filippovich, I. V., et al., *Radiation-induced apoptosis in human ovarian carcinoma cells growing as a monolayer and as multicell spheroids*. Int J Cancer, 1997. 72(5): p. 851-9.
7. Makhija, S., et al., *Taxol-induced bcl-2 phosphorylation in ovarian cancer cell monolayer and spheroids*. Int J Oncol, 1999. 14(3): p. 515-21.
8. Bardies, M., et al., *Use of multi-cell spheroids of ovarian carcinoma as an intraperitoneal radio-immunotherapy model: uptake, retention kinetics and dosimetric evaluation*. Int J Cancer, 1992. 50(6): p. 984-991.
9. Shield, K., et al., *Multicellular spheroids in ovarian cancer metastases: Biology and pathology*. Gynecol Oncol, 2009. 113(1): p. 143-8.
10. Bapat, S. A., *Human ovarian cancer stem cells*. Reproduction, 2010. 140(1): p. 33-41.
11. Fong, M. Y. and S. S. Kakar, *The role of cancer stem cells and the side population in epithelial ovarian cancer*. Histol Histopathol, 2010. 25(1): p. 113-20.
12. Ponnusamy, M. P. and S. K. Batra, *Ovarian cancer: emerging concept on cancer stem cells*. J Ovarian Res, 2008. 1(1): p. 4.
13. Freedman, R. S., et al., *Peritoneal inflammation—A microenvironment for Epithelial Ovarian Cancer (EOC)*. J Transl Med, 2004. 2(1): p. 23.
14. Negus, R. P., et al., *Quantitative assessment of the leukocyte infiltrate in ovarian cancer and its relationship to the expression of C-C chemokines*. Am J Pathol, 1997. 150(5): p. 1723-34.
15. Babior, B. M., et al., *Investigating antibody-catalyzed ozone generation by human neutrophils*. Proc Natl Acad Sci USA, 2003. 100(6): p. 3031-4.
16. Wentworth, P., Jr., et al., *Evidence for antibody-catalyzed ozone formation in bacterial killing and inflammation*. Science, 2002. 298(5601): p. 2195-9.
17. Wentworth, P., Jr., et al., *Evidence for ozone formation in human atherosclerotic arteries*. Science, 2003. 302 (5647): p. 1053-6.
18. Wentworth, P., Jr., et al., *Antibody catalysis of the oxidation of water*. Science, 2001. 293(5536): p. 1806-11.
19. Freeman, B. A., M. C. Sharman, and J. B. Mudd, *Reaction of ozone with phospholipid vesicles and human erythrocyte ghosts*. Arch Biochem Biophys, 1979. 197(1): p. 264-72.
20. Teige, B., T. T. McManus, and J. B. Mudd, *Reaction of ozone with phosphatidylcholine liposomes and the lytic effect of products on red blood cells*. Chem Phys Lipids, 1974. 12(3): p. 153-71.
21. Giamalva, D. H., D. F. Church, and W. A. Pryor, *Effect of bilayer structure on the rates of reaction of ozone with polyunsaturated fatty acids in phosphatidylcholine liposomes*. Chem Res Toxicol, 1988. 1(3): p. 144-5.
22. Parikh, A. N., *Membrane-substrate interface: phospholipid bilayers at chemically and topographically structured surfaces*. Biointerphases, 2008. 3(2): p. FA22.
23. Sanii, B. and A. N. Parikh, *Patterning fluid and elastomeric surfaces using short-wavelength UV radiation and photogenerated reactive oxygen species*. Annu Rev Phys Chem, 2008. 59: p. 411-32.
24. Yu, C., A. N. Parikh, and J. T. Groves, *Direct patterning of membrane-derivatized colloids using in-situ UV-ozone photolithography*. Adv Mater, 2005. 17(12): p. 1477-1480.
25. Steinbeck, M. J., A. U. Khan, and M. J. Karnovsky, *Intracellular singlet oxygen generation by phagocytosing neutrophils in response to particles coated with a chemical trap*. J Biol Chem, 1992. 267(19): p. 13425-33.
26. Steinbeck, M. J., A. U. Khan, and M. J. Karnovsky, *Extracellular production of singlet oxygen by stimulated macrophages quantified using 9,10-diphenylanthracene and perylene in a polystyrene film*. J Biol Chem, 1993. 268(21): p. 15649-54.
27. Piyasena, M. E., et al., *Biosensors based on release of compounds upon disruption of lipid bilayers supported on porous microspheres* Biointerphases, 2008. 3(2): p. 38-49.
28. Chemburu, S., et al., *Biomimetic silica microspheres in biosensing*. Molecules, 2010. 15(3): p. 1932-1957.
29. Troutier, A. L. and C. Ladaviere, *An overview of lipid membrane supported by colloidal particles*. Adv Colloid Interface Sci, 2007. 133(1): p. 1-21.
30. Jemal, A., et al., *Cancer Statistics, 2010*. CA Cancer J Clin, 2010.
31. Auersperg, N., et al., *Ovarian surface epithelium: biology, endocrinology, and pathology*. Endocr Rev, 2001. 22(2): p. 255-88.
32. Hudson, L. G., R. Zeineldin, and M. S. Stack, *Phenotypic plasticity of neoplastic ovarian epithelium: unique cadherin profiles in tumor progression*. Clin Exp Metastasis, 2008. 25(6): p. 643-55.
33. Lengyel, E., *Ovarian Cancer Development and Metastasis*. Am J Pathol, 2010.
34. Heintz, A. P., et al., *Carcinoma of the ovary. FIGO 6th Annual Report on the Results of Treatment in Gynecological Cancer*. Int J Gynaecol Obstet, 2006. 95 Suppl 1: p. S161-S192.
35. Williams, T. I., et al., *Epithelial ovarian cancer: disease etiology, treatment, detection, and investigational gene, metabolite, and protein biomarkers*. J. Proteome Res, 2007. 6(8): p. 2936-2962.
36. Gubbels, J. A., et al., *The detection, treatment, and biology of epithelial ovarian cancer*. J Ovarian Res, 2010. 3: p. 8.
37. Shan, W. and J. Liu, *Inflammation: a hidden path to breaking the spell of ovarian cancer*. Cell Cycle, 2009. 8(19): p. 3107-11.
38. Guruvayoorappan, C., *Tumor versus tumor-associated macrophages: how hot is the link?* Integr Cancer Ther, 2008. 7(2): p. 90-5.
39. Datta, D., et al., *Mechanism for antibody catalysis of the oxidation of water by singlet dioxygen*. Proc Natl Acad Sci USA, 2002. 99(5): p. 2636-41.
40. Lerner, R. A. and A. Eschenmoser, *Ozone in biology*. Proc Natl Acad Sci USA, 2003. 100(6): p. 3013-5.
41. Brinkhorst, J., S. J. Nara, and D. A. Pratt, *Hock cleavage of cholesterol 5alpha-hydroperoxide: an ozone free pathway to the cholesterol ozonolysis products identified in arterial plaque and brain tissue*. J Am Chem Soc, 2008. 130(37): p. 12224-5.
42. Uemi, M., et al., *Generation of cholesterol carboxyaldehyde by the reaction of singlet molecular oxygen [O2 (1Delta(g))] as well as ozone with cholesterol*. Chem Res Toxicol, 2009. 22(5): p. 875-84.
43. Wentworth, A. D., et al., *The ratio of cholesterol 5,6-secosterols formed from ozone and singlet oxygen offers insight into the oxidation of cholesterol in vivo*. Chem Commun (Camb), 2009(21): p. 3098-100.

44. Drahl, C., *Probing For In-Body Ozone: Molecule hunters need better traps to prove that a wily oxygen species is made in the flesh.* Chem & Eng News, 2009. 87(25): p. 40-42.
45. Dedrick, R. L., et al., *Pharmacokinetic rationale for peritoneal drug administration in the treatment of ovarian cancer.* Cancer Treat Rep, 1978. 62(1): p. 1-11.
46. Howell, S. B., *Pharmacologic principles of intraperitoneal chemotherapy for the treatment of ovarian cancer.* Int J Gynecol Cancer, 2008. 18 Suppl 1: p. 20-5.
47. Travagli, V., et al., *A physicochemical investigation on the effects of ozone on blood.* Int J Biol Macromol, 2007. 41(5): p. 504-11.
48. Burgassi, S., et al., *How much ozone bactericidal activity is compromised by plasma components?* J Appl Microbiol, 2009. 106(5): p. 1715-21.
49. Yamashita, K., et al., *Ozone production by amino acids contributes to killing of bacteria.* Proc Natl Acad Sci USA, 2008. 105(44): p. 16912-7.
50. Buranda, T., et al., *Biomimetic molecular assemblies on glass and mesoporous silica microbeads for biotechnology.* Langmuir, 2003. 19(5): p. 1654-1663.
51. Zeineldin, R., et al., *Detection of membrane biointeractions based on fluorescence superquenching.* Langmuir, 2008. 24(8): p. 4125-31.
52. Green, A. E. and P. G. Rose, *Pegylated liposomal doxorubicin in ovarian cancer.* Int J Nanomedicine, 2006. 1(3): p. 229-39.
53. Hawkins, M. J., P. Soon-Shiong, and N. Desai, *Protein nanoparticles as drug carriers in clinical medicine.* Adv Drug Deliv Rev, 2008. 60(8): p. 876-85.
54. Cannistra, S. A., *Evaluating new regimens in recurrent ovarian cancer: how much evidence is good enough?* J Clin Oncol, 2010. 28(19): p. 3101-3103.
55. Zeineldin, R. and L. G. Hudson, *Epithelial cell migration in response to epidermal growth factor.* Methods Mol Biol, 2006. 327: p. 147-158.
56. Edwards, B. S., et al., *High-throughput cytotoxicity screening by propidium iodide staining.* Curr Protoc Cytom, 2007. Chapter 9: p. Unit9 24.
57. Barua, A., et al., *Anti-tumor and anti-ovarian autoantibodies in women with ovarian cancer.* Am J Reprod Immunol, 2007. 57(4): p. 243-9.
58. Luborsky, J. L., et al., *Anti-tumor antibodies in ovarian cancer.* Am J Reprod Immunol, 2005. 54(2): p. 55-62.
59. Piura, B. and E. Piura, *Autoantibodies to tumor-associated antigens in epithelial ovarian carcinoma.* J Oncol, 2009. 2009: p. 581939.

What claimed is:

1. A method of treating a subject who suffers from a cancer, the method comprising intraperitoneally administering to the subject a pharmaceutically effective amount of a nanocarrier composition, comprising a plurality of porous nanoparticulates that are loaded with one or more pharmaceutically active anticancer agents and are encapsulated by and support a lipid bilayer which is disrupted upon contact with a reactive oxygen species, wherein the lipid bilayer comprises 1,2-dimyristoyl-sn-glycero-3-phosphocholine (DMPC).

2. The method of claim 1, wherein:
   (a) the subject suffers from peritoneal cancer and the composition comprising nanocarriers is administered intraperitoneally to the subject's uterus;
   (b) the nanoparticulates are selected from the group consisting of silica nanoparticles, a biodegradable polymer, a sol-gel, a metal-based nanoparticle and an oxide-based nanoparticle;
   (c) subsequent to administration, the lipid bilayer of said nanocarriers is disrupted upon contact with a reactive oxygen species (ROS) selected from the group consisting of ozone ($O_3$), hydrogen peroxide, hypochlorite ion, hydroxyl radical, superoxide anion ($O_2^-$), and peroxynitrite; and
   (d) the nanocarriers' one or more anti-cancer agents are selected from the group consisting of doxorubicin, melphalan, bevacizumab, dactinomycin, cyclophosphamide, amifostine, etoposide, gemcitabine, altretamine, topotecan, a taxane, a platinum based chemotherapeutic agent, and combinations thereof.

3. The method of claim 1, wherein the subject is co-administered one or more additional anti-cancer agents or anti-cancer treatments along with the nanocarrier composition.

4. The method of claim 3, wherein the one or more additional anti-cancer agents or anti-cancer treatments and nanocarrier composition are administered concomitantly to the subject.

5. The method according to claim 1 wherein said composition is administered directly into the cancer/tumor.

6. The method of claim 1, wherein the reactive oxygen species is selected from the group consisting of ozone ($O_3$), hydrogen peroxide, hypochlorite ion, hydroxyl radical, superoxide anion ($O_2^-$), and peroxynitrite.

7. The method of claim 1, wherein the lipid bilayer further comprises one or more lipids selected from the group consisting of phospholipids, cholesterol, a phosphatidyl-choline, a phosphatidyl-serine, a phosphatidyl-diethanolamine, a phosphatidylinosite, a sphingolipid, and an ethoxylated sterol, and mixtures thereof.

8. The method of claim 1, wherein the lipid bilayer further comprises one or more phospholipids selected from the group consisting of 1,2-dioleoyl-3-trimethylammonium-propane (DOTAP), 1-palmitoyl-2-oleoyl-sn-glycero-3-phosphocholine (POPC), egg phosphatidyl-choline (PC), a lipid mixture comprising between about 40 to 60% by weight of one or more unsaturated phosphatidyl-choline, 1,2-dipalmitoyl-sn-glycero-3-phosphocholine (DPPC) [16:0], 1,2-distearoyl-sn-glycero-3-phosphocholine (DSPC) [18:0], 1,2-dioleoyl-sn-glycero-3-phosphocholine, and combinations thereof.

9. The method of claim 1, wherein the lipid bilayer comprises a mixture of (1) egg PC, and (2) 1,2-dimyristoyl-sn-glycero-3-phosphocholine (DMPC).

10. The method of claim 9, wherein the molar concentration of egg PC in the mixture is between about 40% to about 60% of the lipid bilayer.

11. The method of claim 9, wherein the molar concentration of DMPC is between about 40% to about 60% of the lipid bilayer.

12. The method of claim 1, wherein the lipid bilayer further comprises phospholipid selected from the group consisting of monoacyl or diacylphosphoglyceride.

13. The method of claim 1, wherein the lipid bilayer further comprises one or more phospholipids selected from the group consisting of PEG-poly(ethylene glycol)-derivatized distearoylphosphatidylethanolamine (PEG-DSPE), poly(ethylene glycol)-derivatized ceramides (PEG-CER), hydrogenated soy phosphatidylcholine (HSPC), egg phosphatidylcholine (EPC), phosphatidyl ethanolamine (PE), phosphatidyl glycerol (PG), phosphatidyl insitol (PI), monosialogangolioside, spingomyelin (SPM), distearoylphosphatidylcholine (DSPC), and dimyristoylphosphatidylglycerol (DMPG).

14. The method of claim 1, wherein the one or more anticancer agents are selected from the group consisting of doxorubicin, melphalan, bevacizumab, dactinomycin, cyclophosphamide, amifostine, etoposide, gemcitabine, altretamine, topotecan, a taxane, and a platinum based chemotherapeutic agent.

15. A method of treating a subject suffering from peritoneal cancer, the method comprising intraperitoneally administering to the subject a pharmaceutically effective amount of a nanocarrier composition, said nanocarrier composition comprising a plurality of porous silica nanoparticulates that:
   (a) are loaded with one or more pharmaceutically-active agents selected from the group consisting of doxorubicin, melphalan, bevacizumab, dactinomycin, cyclophosphamide, amifostine, etoposide, gemcitabine, altretamine, topotecan, a taxane or a platinum based chemotherapeutic agent, and
   (b) that are encapsulated by and that support a lipid bilayer comprising 1,2-dimyristoyl-sn-glycero-3-phosphocholine (DMPC) to form a nanocarrier;
   wherein subsequent to administration, the lipid bilayer is disrupted in vivo upon contact with a reactive oxygen species (ROS) selected from the group consisting of ozone ($O_3$), hydrogen peroxide, hypochlorite ion, hydroxyl radical, superoxide anion ($O_2^-$), and peroxynitrite.

* * * * *